US008323635B2

(12) United States Patent
Han et al.

(10) Patent No.: US 8,323,635 B2
(45) Date of Patent: Dec. 4, 2012

(54) METHODS OF USING INTERLEUKIN-1 RECEPTOR ANTAGONIST AS A MYELOPROTECTIVE AGENT

(75) Inventors: Wei Han, Shanghai (CN); Jing Zhang, Shanghai (CN); Di Xiang, Shanghai (CN); Shunying Zhu, Shanghai (CN)

(73) Assignee: General Regeneratives, Ltd., Hong Kong (CN)

( * ) Notice: Subject to any disclaimer, the term of this patent is extended or adjusted under 35 U.S.C. 154(b) by 300 days.

(21) Appl. No.: 12/740,264

(22) PCT Filed: Nov. 14, 2007

(86) PCT No.: PCT/CN2007/003215
§ 371 (c)(1), (2), (4) Date: Apr. 28, 2010

(87) PCT Pub. No.: WO2009/062339
PCT Pub. Date: May 22, 2009

(65) Prior Publication Data
US 2010/0254937 A1    Oct. 7, 2010

(51) Int. Cl.
*A61K 45/00* (2006.01)
*A61K 38/18* (2006.01)
*A61K 38/16* (2006.01)
*C07K 14/475* (2006.01)

(52) U.S. Cl. .................. 424/85.2; 514/7.6; 514/21.2

(58) Field of Classification Search ................ None
See application file for complete search history.

(56) References Cited

U.S. PATENT DOCUMENTS

| | | | |
|---|---|---|---|
| 5,075,222 | A | 12/1991 | Hannum et al. |
| 5,739,282 | A | 4/1998 | Colotta et al. |
| 5,747,444 | A | 5/1998 | Haskill et al. |
| 5,858,355 | A | 1/1999 | Glorioso et al. |
| 5,863,769 | A | 1/1999 | Young |
| 5,922,573 | A | 7/1999 | Boraschi et al. |
| 6,054,559 | A | 4/2000 | Young |
| 6,599,873 | B1 | 7/2003 | Sommer et al. |
| 2010/0040603 | A1 | 2/2010 | Han et al. |
| 2010/0080756 | A1 | 4/2010 | Han et al. |

FOREIGN PATENT DOCUMENTS

| | | |
|---|---|---|
| DE | 42 19 626 | 12/1993 |
| WO | WO-91/08285 | 6/1991 |
| WO | WO-91/17184 | 11/1991 |
| WO | WO-91/17249 | 11/1991 |
| WO | WO-92/16221 | 10/1992 |
| WO | WO-94/06457 | 3/1994 |
| WO | WO-94/20517 | 9/1994 |
| WO | WO-94/21235 | 9/1994 |
| WO | WO-94/21275 | 9/1994 |
| WO | WO-96/12022 | 4/1996 |
| WO | WO-97/28828 | 8/1997 |
| WO | WO-99/36541 | 7/1999 |
| WO | WO-99/51744 | 10/1999 |
| WO | WO-01/89549 | 11/2001 |
| WO | WO-02/36152 | 5/2002 |
| WO | WO-2006/094971 | 9/2006 |

OTHER PUBLICATIONS

Chudgar et al., "Recombinant Human Interleukin-1 Receptor Antagonist Protects Early Myeloid Progenitors in a Murine Model of Cyclophosphamide-Induced Myelotoxicity," Blood, vol. 85, No. 9, May 1, 1995, pp. 2393-2401.
Cohen et al., "Treatment of rheumatoid arthritis with anakinra, a recombinant human interleukin-I receptor antagonist, in combination with methotrexate," Arthritis & Rheumatism, vol. 46, No. 3, Mar. 2002, pp. 614-624.
Cohen, "The use of anakinra, an interleukin-1 receptor antagonist, in the treatment of rheumatoid arthritis," Rheum Dis. Clin. N. Am., vol. 30, 2004, pp. 365-380.
Furst, "Anakinra: review of recombinant human interleukin-I receptor antagonist in the treatment of rheumatoid arthritis," Clinical Therapeutics, 2004, vol. 26, No. 12, pp. 1960-1975.
Han, W. et al., "Local signals in stem cell-based bone marrow regeneration," Cell Research, vol. 16, pp. 189-195, 2006.
International Search Report and Written Opinion for PCT/CN2007/003215 dated Aug. 14, 2008.
Jinquan, T. et al., "CXC chemokine receptor 3 expression on CD34+ hematopoietic progenitors from human cord blood induced by granulocyte-macrophage colony-stimulating factor: chemotaxis and adhesion induced by its ligands, interferon y-inducible protein 10 and monokine induced by interferon y," Blood Journal, vol. 96, No. 4, pp. 1230-1238, Aug. 15, 2000.
Lazzeri, E. et al., CXCR3-binding Chemokines: Novel Multifunctional Therapeutic Targets, Current Drug Targets—Immune, Endocrine & Metabolic Disorders, vol. 5, pp. 109-118, 2005.
Liao, F. et al., "Human Mig Chemokine: Biochemical and Functional Characterization," J. Exp. Med., vol. 182, pp. 1301-1314, Nov. 1995.
Rollins, B.J., "Chemokines," Blood Journal, vol. 90, No. 3, pp. 909-928, 1997.
Ruehlmann, J. M. et al., "MIG (CXCL9) Chemokine Gene Therapy Combines with Antibody-Cytokine Fusion Protein to Suppress Growth and Dissemination of Murine Colon Carcinoma," Cancer Research, vol. 61, pp. 8498-8503, Dec. 1, 2001.
Zhang, R. et al., "Combination of MIG (CXCL9) chemokine gene therapy with low-dose cisplatin improves therapeutic efficacy against murine carcinoma," Gene Therapy, vol. 13, pp. 1263-1271, 2006.
Database Biosis (Online); Biosciences Information Service; Philadelphia, PA (1996); Jovic, G., et al.; "The effect of IL-1 receptor antagonist on the proliferation of hematopoietic profenitor cells in regenerating bone marrow"; (Abstract only) Database Accession No. PREV199698827004 (2 pgs.).
Database Biosis (Online); Biosciences Information Service; Philadelphia, PA, (1996); Neta Ruth, et al.; "Contrasting Mechanisms of the myeloprotective effects of interleukin-1 against ionizing radiation and cytotoxic 5-fluorouracil"; (Abstract only) Database Accession No. PREV199699013367 (2 pgs.).
Supplementary European Search Report; In re European Patent Application No. 07816824.2; Dated: Jul. 20, 2011; Applicant: General Regeneratives Limited, (9pgs.).
Chinese Office Action; Chinese Appl. No. 200780102187.4; Issued: Jan. 18, 2012; Applicant: General Regeneratives Limited; (6 pgs.) (English Translation).
First Examination Report; European Application No. 07816824.2; Issued: Mar. 12, 2012; Applicant: General Regeneratives Limited; (5 pgs.).

*Primary Examiner* — Robert Landsman
(74) *Attorney, Agent, or Firm* — Foley & Lardner LLP

(57) ABSTRACT

The present invention relates to uses of interleukin-1 receptor antagonist (IL-1Ra) in promoting bone marrow regeneration, increasing peripheral white blood cells, and increasing platelet levels in subjects if administered prior to treatment with chemotherapeutic agents. Thus, particular embodiments of the invention are directed to uses of IL-1Ra as an adjuvant or ancillary therapy to alleviate the hematopoietic toxicities associated with chemotherapy.

16 Claims, 16 Drawing Sheets

CONTROL rMuIL-1Ra

SEQUENCE LISTING

```
<160> NUMBER OF SEQ ID NOS: 7

<210> SEQ ID NO 1
<211> LENGTH: 177
<212> TYPE: PRT
<213> ORGANISM: Homo sapiens

<400> SEQUENCE: 1

Met Glu Ile Cys Arg Gly Leu Arg Ser His Leu Ile Thr Leu Leu Leu
1               5                   10                  15

Phe Leu Phe His Ser Glu Thr Ile Cys Arg Pro Ser Gly Arg Lys Ser
            20                  25                  30

Ser Lys Met Gln Ala Phe Arg Ile Trp Asp Val Asn Gln Lys Thr Phe
        35                  40                  45

Tyr Leu Arg Asn Asn Gln Leu Val Ala Gly Tyr Leu Gln Gly Pro Asn
    50                  55                  60

Val Asn Leu Glu Glu Lys Ile Asp Val Val Pro Ile Glu Pro His Ala
65                  70                  75                  80

Leu Phe Leu Gly Ile His Gly Gly Lys Met Cys Leu Ser Cys Val Lys
                85                  90                  95

Ser Gly Asp Glu Thr Arg Leu Gln Leu Glu Ala Val Asn Ile Thr Asp
            100                 105                 110

Leu Ser Glu Asn Arg Lys Gln Asp Lys Arg Phe Ala Phe Ile Arg Ser
        115                 120                 125

Asp Ser Gly Pro Thr Thr Ser Phe Glu Ser Ala Ala Cys Pro Gly Trp
    130                 135                 140

Phe Leu Cys Thr Ala Met Glu Ala Asp Gln Pro Val Ser Leu Thr Asn
145                 150                 155                 160

Met Pro Asp Glu Gly Val Met Val Thr Lys Phe Tyr Phe Gln Glu Asp
                165                 170                 175

Glu

<210> SEQ ID NO 2
<211> LENGTH: 153
<212> TYPE: PRT
<213> ORGANISM: Mus musculus

<400> SEQUENCE: 2

Met Arg Pro Ser Gly Lys Arg Pro Cys Lys Met Gln Ala Phe Arg Ile
1               5                   10                  15

Trp Asp Thr Asn Gln Lys Thr Phe Tyr Leu Arg Asn Asn Gln Leu Ile
```

-continued

```
                    20                  25                  30
Ala Gly Tyr Leu Gln Gly Pro Asn Ile Lys Leu Glu Glu Lys Ile Asp
            35                  40                  45

Met Val Pro Ile Asp Leu His Ser Val Phe Leu Gly Ile His Gly Gly
 50                  55                  60

Lys Leu Cys Leu Ser Cys Ala Lys Ser Gly Asp Asp Ile Lys Leu Gln
 65                  70                  75                  80

Leu Glu Glu Val Asn Ile Thr Asp Leu Ser Lys Asn Lys Glu Glu Asp
                85                  90                  95

Lys Arg Phe Thr Phe Ile Arg Ser Glu Lys Gly Pro Thr Thr Ser Phe
            100                 105                 110

Glu Ser Ala Ala Cys Pro Gly Trp Phe Leu Cys Thr Thr Leu Glu Ala
        115                 120                 125

Asp Arg Pro Val Ser Leu Thr Asn Thr Pro Glu Glu Pro Leu Ile Val
        130                 135                 140

Thr Lys Phe Tyr Phe Gln Glu Asp Gln
145                 150
```

<210> SEQ ID NO 3
<211> LENGTH: 28
<212> TYPE: DNA
<213> ORGANISM: Artificial sequence
<220> FEATURE:
<223> OTHER INFORMATION: Synthetic primer

<400> SEQUENCE: 3
catgccatgg cacgcccttc tgggaaaa                                         28

<210> SEQ ID NO 4
<211> LENGTH: 32
<212> TYPE: DNA
<213> ORGANISM: Artificial sequence
<220> FEATURE:
<223> OTHER INFORMATION: Synthetic primer

<400> SEQUENCE: 4
cgggatccct attggtcttc ctggaagtag aa                                    32

<210> SEQ ID NO 5
<211> LENGTH: 34
<212> TYPE: DNA
<213> ORGANISM: Artificial sequence
<220> FEATURE:
<223> OTHER INFORMATION: Synthetic primer

<400> SEQUENCE: 5
ggaattccat atgcgaccct ctgggagaaa atcc                                  34

<210> SEQ ID NO 6
<211> LENGTH: 32
<212> TYPE: DNA
<213> ORGANISM: Artificial sequence
<220> FEATURE:
<223> OTHER INFORMATION: Synthetic primer

<400> SEQUENCE: 6
cgcggatcct tactcgtcct cctggaagta ga                                    32

<210> SEQ ID NO 7
<211> LENGTH: 153
<212> TYPE: PRT
<213> ORGANISM: Homo sapiens -continued

```
<400> SEQUENCE: 7

Met Arg Pro Ser Gly Arg Lys Ser Ser Lys Met Gln Ala Phe Arg Ile
1               5                   10                  15

Trp Asp Val Asn Gln Lys Thr Phe Tyr Leu Arg Asn Asn Gln Leu Val
            20                  25                  30

Ala Gly Tyr Leu Gln Gly Pro Asn Val Asn Leu Glu Glu Lys Ile Asp
            35                  40                  45

Val Val Pro Ile Glu Pro His Ala Leu Phe Leu Gly Ile His Gly Gly
        50                  55                  60

Lys Met Cys Leu Ser Cys Val Lys Ser Gly Asp Glu Thr Arg Leu Gln
65                  70                  75                  80

Leu Glu Ala Val Asn Ile Thr Asp Leu Ser Glu Asn Arg Lys Gln Asp
                85                  90                  95

Lys Arg Phe Ala Phe Ile Arg Ser Asp Ser Gly Pro Thr Thr Ser Phe
            100                 105                 110

Glu Ser Ala Ala Cys Pro Gly Trp Phe Leu Cys Thr Ala Met Glu Ala
            115                 120                 125

Asp Gln Pro Val Ser Leu Thr Asn Met Pro Asp Glu Gly Val Met Val
        130                 135                 140

Thr Lys Phe Tyr Phe Gln Glu Asp Glu
145                 150
```

METHODS OF USING INTERLEUKIN-1 RECEPTOR ANTAGONIST AS A MYELOPROTECTIVE AGENT

CROSS-REFERENCE TO RELATED APPLICATIONS

The present application is a U.S. national stage application claiming the benefit of International Application No. PCT/CN2007/003215, filed on Nov. 14, 2007, the contents of which is incorporated herein by reference in its entirety.

FIELD OF THE INVENTION

The present invention relates generally to methods of protecting a subject against the harmful effects of chemotherapy. In particular, the present invention relates to administration of an interleukin-1 receptor antagonist to a subject, thereby reducing the myelotoxicity of chemotherapeutic agents.

BACKGROUND OF THE INVENTION

The following description is provided to assist the understanding of the reader. None of the information provided or references cited is admitted to be prior art to the present invention.

Hematopoiesis is a complex process in which hematopoietic stem cells are capable of self-renewal to maintain a long-term supply of progenies and are stimulated to differentiate into multiple lineages by various growth factors. It is assumed that the majority of hematopoietic stem cells are in the quiescent ($G_0$) phase of the cell cycle, and only a few actively cycling hematopoietic stem cells supply all the hematopoietic cells at a given time. This concept is supported by evidence that quiescent hematopoietic stem cells are resistant to the cytotoxic effects of 5-fluorouracil (5-FU), whereas most of the cycling counterparts are sensitive to 5-FU, thus resulting in myelosuppression.

Myelosuppression is the most common adverse effect of cytotoxic chemotherapy and is a major limiting factor in the clinical treatment of cancer. Therefore, promotion of hematopoiesis remains an extremely important challenge in cancer therapy. A large number of cytokines have been screened for their chemoprotective potential. Administration of recombinant colony-stimulating factors, such as granulocyte-macrophage colony stimulating factor (GM-CSF), granulocyte colony stimulating factor (G-CSF), and stem cell factor (SCF), alleviates chemotherapy-induced myelotoxicity augmenting proliferation of hematopoietic progenitor cells in the bone marrow and accelerates the recovery of peripheral blood cells.

There are three members of the interleukin-1 (IL-1) gene family: IL-1α, IL-1β, and IL-1 receptor antagonist (IL-1Ra). IL-1α and IL-1β are receptor agonists and IL-1Ra is a specific receptor antagonist. IL-1α and IL-1β are synthesized as 31 kDa precursors. Processing of IL-1α and IL-1β to "mature" forms of 17 kDa requires specific cellular proteases. IL-1Ra is the first described naturally occurring specific receptor antagonist of any cytokine or hormone-like molecule. IL-1Ra is a member of the IL-1 family that binds to IL-1 receptors but does not induce any intracellular response. Two structure variants of IL-1Ra have previously been described: a 17 kDa form that is secreted from monocytes, macrophages, neutrophils, and other cells (sIL-1Ra) and a 18 kDa form that remains in the cytoplasm of keratinocytes and other epithelial cells, monocytes, and fibroblasts (icIL-1Ra). Secretory IL-1Ra (sIL-1Ra) is synthesized as a 177 amino acid protein, with cleavage of a 25 amino acid leader sequence prior to secretion as a variably glycosylated 152 amino acid protein.

SUMMARY OF THE INVENTION

The invention provides methods for using IL-1Ra to protect hematopoietic cells and other bone marrow cells from the harmful effects of chemotherapy. The invention also provides treatment methods for cancer. The methods are based on the myelosuppressive action of IL-1Ra. The invention offers novel ways to enhance the recovery of the suppressed hematopoietic system as part of a regimen of chemotherapy, particularly in the treatment of cancer.

In one aspect, the present invention provides methods for providing myeloprotection to a subject in need of chemotherapy comprising administering an effective amount of interleukin-1 receptor antagonist (IL-1Ra) to the subject prior to administering a chemotherapeutic agent to the subject, wherein following the administration of the chemotherapeutic agent, the subject has increased bone marrow cell density, increased platelet level, or increased peripheral white blood cell level compared to a subject not administered the interleukin-1 receptor antagonist.

In one embodiment, the IL-1Ra is administered to a subject near the time a subject receives a treatment with associated hematopoietic toxicities, e.g., chemotherapy. For example, this may include administration of the IL-1Ra at any reasonable time period either before the administration of the treatment, such as one month, three weeks, two weeks, one week, several days, one day, 20 hours, several hours, one hour or minutes. Further administration of IL-1Ra may occur simultaneously with the treatment and/or after the treatment. In one embodiment the IL-1Ra is administered once a day for one to five days prior to the subject receiving a chemotherapeutic agent. In another embodiment, the IL-1Ra is administered once a day for two to five days prior to the subject receiving the chemotherapeutic agent.

In various embodiments, the IL-1Ra is administered through any route suitable for delivery of the agent to the subject. In one embodiment, the IL-1Ra is administered subcutaneously. The effective amount of IL-1Ra to provide a therapeutic benefit may be determined by those of skill in the art. In one embodiment, the effective amount is from 0.1 to 10 mg of interleukin-1 receptor antagonist per kg body weight of the subject. In another embodiment, the effective amount is from 0.5 to 1.5 mg of interleukin-1 receptor antagonist per kg body weight of the subject.

In accordance with the methods of the invention, biologically active fragments, variants, or homologues of IL-1Ra may be used. In one embodiment, the IL-1Ra is human IL-1Ra. In a particular embodiment, the IL-1Ra has an amino acid sequence according to SEQ ID NO: 1. In certain embodiments, the IL-1Ra may be a variant of SEQ ID NO:1 having at least 80%, at least 85%, at least 90%, at least 95%, at least 96%, at least 97%, at least 98%, or at least 99% sequence identity to SEQ ID NO: 1.

In certain embodiments, IL1-Ra is administered to a subject prior to the subject receiving a chemotherapeutic agent. In some embodiments, the chemotherapeutic agent may be a cell cycle-specific chemotherapeutic agent, e.g., 5-fluorouracil, Ara-C, vinblastine, and methotrexate. In other embodiments, the chemotherapeutic agent is cell cycle non-specific, e.g., cyclophosphamide, doxorubicin, cisplatin, and busulfan.

In one embodiment, the methods of the present invention further comprise administering a hematopoietic growth factor to the subject following the chemotherapeutic agent. Examples of growth factors include, but are not limited to GM-CSF or G-CSF.

In one embodiment, the methods of the present invention further comprise administering an additional myelosuppressive agent to the subject prior to the subject receiving a chemotherapeutic agent. Examples of an additional myelosuppressive agent is CCL3 or CXCL9.

BRIEF DESCRIPTION OF THE DRAWINGS

FIG. 1A shows IL-1Ra in crude extracts of uninduced (lane 1) and induced (lane 2) *E. coli* cells. FIG. 1B shows the presence of the IL-1Ra in the pellet fraction (lane 2) compared to the supernatant (lane 1). FIG. 1C shows protein samples of anion exchange chromatography fractions near the peak UV absorbance.

FIG. 14A shows IL-1Ra expression in *E. coli* cells (Lane 0: markers; Lane 1: uninduced cells; Lane 3: inclusion bodies; Lane 4: supernatant after sonication; Lane 5: solubilized inclusion bodies; Lane 6: refolded rhIL-1Ra; Lane 7: ammonium-precipitated rhIL-1Ra; Lane 8: solubilized rhIL-1Ra following ammonium sulfate precipitation). FIG. 14B shows the presence of the partially-purified IL-1Ra (Lane 0: markers; Lane 1: refolded rhIL-1Ra; Lane 2: fractions collected after DEAE-sepharose purification; Lane 3: rhIL-1Ra before Q-Sepharose purification; Lane 4: rHIL-1Ra after Q-Sepharose purification. FIG. 14C shows the purified IL-1Ra (Lane 0: markers; Lane 1: flow through solution after Q-Sepharose purification; Lane 2: rhIL-1Ra before Q-Sepharose purification; Lane 3: rhIL-1Ra after Q-Sepharose purification).

DETAILED DESCRIPTION

Figure 1A:
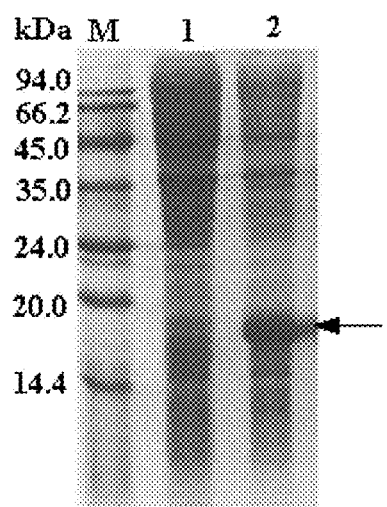
FIGS. 1A-C shows SDS-PAGE analysis of recombinant murine IL-1Ra polypeptides.

The present invention generally relates to methods of preventing myelotoxicity associated with chemotherapy, thereby providing a chemoprotective effect. In particular, the methods of the invention comprise administration of IL-1Ra to promote bone marrow regeneration, increase peripheral white blood cells, increase platelets level, and enhance survival of subjects, if administered prior to treatment with a chemotherapeutic agent, such as 5-fluorouracil (5-FU). Compositions and methods are presented for the treatment of cancer.

Definitions. In the description that follows, a number of terms are utilized extensively. Definitions are herein provided to facilitate understanding of the invention. The terms defined below are more fully defined by reference to the specification as a whole.

Units, prefixes, and symbols may be denoted in their accepted SI form. Unless otherwise indicated, nucleic acids are written left to right in 5' to 3' orientation; amino acid sequences are written left to right in amino to carboxy orientation. Amino acids may be referred to herein by either their commonly known three letter symbols or by the one-letter symbols recommended by the IUPAC-IUBMB Nomenclature Commission. Nucleotides, likewise, may be referred to by their commonly accepted single-letter codes.

The terms "a" and "an" as used herein mean "one or more" unless the singular is expressly specified.

As used herein, the "administration" of an agent or drug to a subject or subject includes any route of introducing or delivering to a subject a compound to perform its intended function. Administration can be carried out by any suitable route, including orally, intranasally, parenterally (intravenously, intramuscularly, intraperitoneally, or subcutaneously), rectally, or topically. Administration includes self-administration and the administration by another. It is also to be appreciated that the various modes of treatment or prevention of medical conditions as described are intended to mean "substantial", which includes total but also less than total treatment or prevention, and wherein some biologically or medically relevant result is achieved.

As used herein, the term "amino acid" includes naturally-occurring amino acids and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally-occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid. Amino acids can be referred to herein by either their commonly known three letter symbols or by the one-letter symbols recommended by the IUPAC-IUB Biochemical Nomenclature Commission. Nucleotides, likewise, can be referred to by their commonly accepted single-letter codes.

The term "bone marrow cells" generally refers to cells that reside in and/or home to the bone marrow compartment of a mammal. Included in the term "bone marrow cells" is not only cells of hematopoietic origin, including but not limited to hematopoietic repopulating cells, hematopoietic stem cell and/or progenitor cells, but any cells that may be derived from bone marrow, such as endothelial cells, mesenchymal cells, bone cells, neural cells, supporting cells (stromal cells), including but not limited to the associated stem and/or progenitor cells for these and other cell types and lineages.

The term "chemotherapy" refers to any therapy that includes natural or synthetic chemotherapeutic agents now known or to be developed in the medical arts. Examples of chemotherapeutic agents include the numerous cancer drugs that are currently available. However, chemotherapy also includes any drug, natural or synthetic, that is intended to treat a disease state. In certain embodiments of the invention, chemotherapy may include the administration of several state of the art drugs intended to treat the disease state. Examples include chemotherapy with docetaxel, cisplatin, 5-fluorouracil, fludarabine and bendamustine.

As used herein, the term "effective amount" or "pharmaceutically effective amount" or "therapeutically effective amount" or "prophylactically effective amount" of a composition, is a quantity sufficient to achieve a desired therapeutic and/or prophylactic effect, e.g., an amount which results in the prevention of, or a decrease in, the symptoms associated with a disease that is being treated, e.g., a cancer. The amount of a composition of the invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds. In the methods of the present invention, IL-1Ra compositions may be administered to a subject prior to administration of a chemotherapeutic agent. An effective amount of IL-1Ra may include an amount in which the myelosuppressive effects of chemotherapy are ameliorated.

As used herein, "expression" includes, but is not limited to one or more of the following: transcription of the gene into precursor mRNA; splicing and other processing of the precursor mRNA to produce mature mRNA; mRNA stability; translation of the mature mRNA into protein (including codon usage and tRNA availability); and glycosylation and/or other modifications of the translation product, if required for proper expression and function.

The term "hematopoietic cells" refers to morphologically recognizable and functionally capable cells circulating in blood, including mature hematopoietic cells and hematopoietic stem and progenitor cells. Mature hematopoietic cells include erythrocytes, macrophages or monocytes, neutrophilic, eosinophilic, and basophilic granulocytes, B-, T, non B-, non T-lymphocytes, and platelets. These mature hematopoietic cells derive from and are replaced, on demand, by morphologically recognizable dividing precursor cells for the respective lineages such as erythroblasts for the erythrocyte series, myeloblasts, promyelocytes and myelocytes for the monotyte/macrophage and granulocyte series, and megakaryocytes for the platelets.

The precursor cells derive from more primitive cells that can simplistically be divided into two major subgroups: stem cells and progenitor cells. The definitions of stem and progenitor cells are operational and depend on functional, rather than on morphological, criteria. Stem cells have extensive self-renewal or self-maintenance capacity, a necessity since an absence or depletion of these cells could result in the complete depletion of one or more cell lineages or cell types, events that would lead within a short time to disease and death. Some of the stem cells differentiate upon need, but some stem cells or their daughter cells produce other stem cells to maintain the precious pool of these cells. Thus, in addition to maintaining their own kind, pluripotential stem cells, or hematopoietic repopulating cells, are capable of differentiation into several sub-lines of progenitor cells with more limited self-renewal capacity or no self-renewal capacity. These progenitor cells ultimately give rise to the morphologically recognizable precursor cells. The progenitor cells are capable of proliferating and differentiating along one, or more than one, of the myeloid differentiation pathways (Lajtha, L. G., 1979, *Blood Cells* 5: 447).

The term "interleukin-1 receptor antagonist" or "IL-1Ra" refers to a 17-kDa polypeptide that is produced by several cell types in mammals, including adherent monocytes. IL-1Ra is a human protein that acts as an inhibitor of interleukin-1 activity and is a member of the IL-1 family, which also includes IL-1α and IL-1β. A non-exclusive, non-limiting, non-exhaustive list of IL-1 receptor antagonists includes intracellular IL-1Ra (icIL-1Ra), IL-1Raβ (see, e.g., PCT Publication No. WO 99/36541), IL-1Ra variants, and IL-1Ra derivatives. Certain IL-1Ra receptor antagonists, including IL-1Ra and variants and derivatives thereof, as well as methods of making and using them, are described, e.g., in U.S. Pat. No. 5,075,222; U.S. Pat. No. 6,599,873 B1; U.S. Pat. No. 5,863,769; U.S. Pat. No. 5,858,355; U.S. Pat. No. 5,739,282; U.S. Pat. No. 5,922,573; U.S. Pat. No. 6,054,559; WO 91/08285; WO 91/17184; WO 91/17249; AU 9173636; WO 92/16221; WO 93/21946; WO 94/06457; WO 94/21275; FR 2706772; WO 94/21235; DE 4219626; WO 94/20517; WO 96/22793; WO 96/12022; WO 97/28828; WO 99/36541; WO 99/51744. An IL-1 receptor antagonist may be glycosylated or non-glycosylated. An exemplary IL-1Ra includes, but is not limited to, a polypeptide comprising an amino acid sequence as set forth in SEQ ID NO: 1 and fragments, variants, and derivatives of such a polypeptide that have an antagonist activity for the IL-1 receptor.

TABLE 1

Amino acid sequence of hIL-1Ra (SEQ ID NO: 1)

MEICRGLRSHLITLLLFLFHSETICRPSGRKSSKMQAFRIWDVNQKTFYL

RNNQLVAGYLQGPNVNLEEKIDVVPIEPHALFLGIHGGKMCLSCVKSGDE

TRLQLEAVNITDLSENRKQDKRFAFIRSDSGPTTSFESAACPGWFLCTAM

EADQPVSLTNMPDEGVMVTKFYFQEDE

As used herein, the terms "identical" or percent "identity", when used in the context of two or more nucleic acids or polypeptide sequences, refers to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site). Such sequences are then said to be "substantially identical." This term also refers to, or can be applied to, the complement of a test sequence. The term also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An "isolated" or "purified" polypeptide or biologically-active portion thereof is substantially free of cellular material or other contaminating polypeptides from the cell or tissue source from which a polypeptide, e.g., the IL-1Ra polypeptide, is derived, or substantially free from chemical precursors or other chemicals when chemically synthesized. For example, an isolated IL-1Ra polypeptide would be free of materials that would interfere with therapeutic uses of the agent. Such interfering materials may include enzymes, hormones and other proteinaceous and nonproteinaceous solutes.

The term "myeloprotective effect" refers to the effect that substantially arises from the administration of the IL-1Ra compositions of the invention to a subject prior to the administration of a chemotherapeutic agent. This protective effect can be manifested in a subject as an increased bone marrow cell density, increased level of platelets, or increased level peripheral white blood cells compared to a subject not receiving the IL-1Ra composition prior to receiving the chemotherapeutic agent.

The terms "myelotoxicity" or "hematopoietic toxicity" refer to a toxicity that substantially arises from the administration of a treatment to a subject that adversely affects the hematopoietic system of the subject. This adverse effect can be manifested in the subject broadly whereby many hematopoietic cell types are altered from what is considered to be normal levels, as a result of the treatment, or as a result of the treatment and the disease state combined, or the adverse effect can be manifested in the subject more specifically whereby only one or a few hematopoietic cell types are altered from what is considered to be normal levels, as a result of the treatment, or as a result of the treatment and the disease state combined.

As used herein, the term "pharmaceutically-acceptable carrier" is intended to include any and all solvents, dispersion media, coatings, antibacterial and antifungal compounds, isotonic and absorption delaying compounds, and the like, compatible with pharmaceutical administration.

As used herein, the term "polynucleotide" or "nucleic acid" means any RNA or DNA, which may be unmodified or modified RNA or DNA. Polynucleotides include, without limitation, single- and double-stranded DNA, DNA that is a mixture of single- and double-stranded regions, single- and double-stranded RNA, RNA that is mixture of single- and double-stranded regions, and hybrid molecules comprising DNA and RNA that may be single-stranded or, more typically, double-stranded or a mixture of single- and double-stranded regions. In addition, polynucleotide refers to triple-stranded regions comprising RNA or DNA or both RNA and DNA. The term polynucleotide also includes DNAs or RNAs containing one or more modified bases and DNAs or RNAs with backbones modified for stability or for other reasons. In a particular embodiment, the polynucleotide contains polynucleotide sequences encoding IL-1Ra, or a biologically active fragment or variant thereof.

As used herein, the terms "polypeptide", "peptide" and "protein" are used interchangeably herein to mean a polymer comprising two or more amino acids joined to each other by peptide bonds or modified peptide bonds, i.e., peptide isosteres. Polypeptide refers to both short chains, commonly referred to as peptides, glycopeptides or oligomers, and to longer chains, generally referred to as proteins. Polypeptides may contain amino acids other than the 20 gene-encoded amino acids. Polypeptides include amino acid sequences modified either by natural processes, such as post-translational processing, or by chemical modification techniques that are well known in the art. Such modifications are well described in basic texts and in more detailed monographs, as well as in a voluminous research literature. In a particular embodiment, the polypeptide contains polypeptide sequences from IL-1Ra, or a biologically active fragment or variant thereof.

As used herein, the term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the material is derived from a cell so modified. Thus, e.g., recombinant cells express genes that are not found within the native (non-recombinant) form of the cell or express native genes that are otherwise abnormally expressed, under expressed or not expressed at all.

As used herein, the term "subject" refers to an organism administered one or more compositions of the invention. Typically, the subject is a mammal, such as an animal, e.g., domestic animals (e.g., dogs, cats and the like), farm animals (e.g., cows, sheep, pigs, horses and the like) and laboratory animals (e.g., monkey, rats, mice, rabbits, guinea pigs and the like). In preferable embodiments, the subject is a human.

As used herein, the term "substitution" is one of mutations that is generally used in the art. Those substitution variants have at least one amino acid residue in the IL-1Ra polypeptide molecule replaced by a different residue. "Conservative substitutions" typically provide similar biological activity as the unmodified polypeptide sequence from which the conservatively modified variant was derived. Conservative substitutions typically include the substitution of one amino acid for another with similar characteristics. Conservative substitution tables providing functionally similar amino acids are well known in the art. For example, the following six groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic (Cationic): Arginine (R), Lysine (K), Histidine (H); Acidic (Anionic): Aspartic acid (D), Glutamic acid (E); Amide: Asparagine (N), Glutamine (Q).

As used herein, the terms "treating" or "treatment" or "alleviation" refers to both therapeutic treatment and prophylactic or preventative measures, wherein the object is to prevent or slow down (lessen) the targeted pathologic condition or disorder. A subject is successfully "treated" for a cancer, if after receiving a therapeutic amount of the IL-1Ra compositions and a chemotherapeutic agent according to the methods of the present invention, the subject shows observable and/or measurable reduction in or absence of one or more signs and symptoms of the cancer, e.g., reduction in the number of cancer cells or absence of the cancer cells; reduction in the tumor size; inhibition (i.e., slow to some extent and preferably stop) of tumor metastasis; inhibition, to some extent, of tumor growth; increase in length of remission, and/or relief to some extent, one or more of the symptoms associated with the specific cancer; reduced morbidity and mortality, and improvement in quality of life issues.

Methods of the Present Invention

The present invention relates to therapeutic methods for treating diseases and disorders in which increased amounts of hematopoietic cells are desirable (e.g., conditions where the recommended therapy has associated myelotoxicities, thus leading to reduced numbers of one or more hematopoietic cell types or lineages) by administration of IL-1Ra, or biologically active fragments or variants thereof. Thus, embodiments of the invention provide methods of alleviating or treating various hematopoietic cell deficiencies, including deficiencies in hematopoietic repopulating cells, progenitor and stem cells, by the direct administration of IL-1Ra to a subject.

In one aspect of the invention, methods are disclosed for treating a disease state in a subject by administering a treatment to the mammal that is intended to target the disease state, where the treatment has an associated hematopoietic toxicity, in conjunction with the administration of one or more therapeutically effective dose(s) of IL-1Ra prior to the time of administration of the treatment. One effect of the administration of IL-1Ra to the subject is reduction of the hematopoietic toxicity of the treatment, thus permitting high-dose and dose dense protocols to be utilized in designed a particular subject's therapeutic regimen.

Chemotherapy and radiation therapy used in the treatment of cancer and certain immunological disorders can cause pancytopenias or combinations of anemia, neutropenia and thrombocytopenia. Thus, the increase or replacement of hematopoietic cells is often crucial to the success of such treatments. For a general discussion of hematological disorders and their causes, see, e.g., "Hematology" in *Scientific American Medicine*, E. Rubenstein and D. Federman, eds., Volume 2, chapter 5, Scientific American, New York (1996).

IL-1Ra can be administered at any point in time near the administration of the treatment to yield a desired therapeutic effect. In one embodiment, IL-1Ra is administered to a subject prior to administration of the treatment, for example, from 1 to 2 days prior, from 1 to 3 days prior, from 1 to 4 days prior, from 1 to 5 days prior or from 1 to 10 days prior to the administration of the treatment. During this period, administration may occur once a day or more than once a day. An overall benefit of practicing this embodiment of the invention is that the administration of IL-1Ra to the mammal reduces or decreases the hematopoietic toxicity of the treatment, and as a consequence alters the limiting toxic dosage of the various treatment modalities. In most cases, the dosage of the treatment can be increased relative to a subject not administered IL-1Ra prior to treatment.

In one embodiment, IL-1Ra is administered to a subject before and after administration of the treatment. For example, the subject may be administered IL-1Ra from 1 to 2 days prior and from 1 to 2 days after treatment, optionally including the day of treatment. In another example, the subject may be administered IL-1Ra from 1 to 5 days prior and from 1 to 5 days after treatment, optionally including the day of treatment. In another example, the subject may be administered IL-1Ra from 1 to 10 days prior and from 1 to 10 days after treatment, optionally including the day of treatment. An overall benefit of practicing this embodiment of the invention is that the administration of IL-1 to the mammal reduces or decreases the hematopoietic toxicity of the treatment, and as a consequence alters the limiting toxic dosage of the various treatment modalities.

In one aspect, the disease to be treated is a cancer. The subject who receives the IL1-Ra therapy is generally one who is scheduled for chemotherapy, or can be a person who is about to be exposed to, or is at risk for exposure to, a significant amount of bone marrow damaging radiation or chemicals. For example, the subject can be a human patient or an animal who has been diagnosed with a cancer for which chemotherapy or radiation therapy is considered to be an advantageous treatment. Most types of cancer can be treated with either chemotherapy or radiation therapy. Preferred are cancers that have metastasized, or are suspected of having metastasized, and cannot be entirely removed from the body by surgery. A variety of animal models for such cancers are known, which can be used to explore the effectiveness of various agents of the invention, as well as administration and dosing protocols. Agents of the present invention are useful for treating a cancer selected from the group consisting of breast, ovarian, colorectal, gastric, lung, kidney, bladder, prostate, uterine, thyroid, pancreatic, cervical, esophageal, mesothelioma, head and neck, hepatocellular, melanoma, brain, vulval, testicular, sarcoma, intestine, skin, leukemia, and lymphoma cancer. A preferred cancer is breast cancer, melanoma, lung cancer, mesothelioma, thyroid cancer, colon cancer or liver cancer.

The administration of an effective amount of IL-1Ra is accompanied by an improvement of bone marrow condition following the chemotherapy, radiotherapy, or other damaging agent exposure. Bone marrow condition for a subject has improved if one or more of the following occurs: the density of bone marrow cells is greater than if no administration of IL1-Ra was made; the density of progenitor cells or stem cells in bone marrow is greater than if no administration was made; the mass of bone marrow tissue is greater than if no administration was made; or the rate of bone marrow cell proliferation is greater than if no administration was made. The determination of effectiveness can be made at any time following therapy with a chemical or radiation agent. For example, the determination of effectiveness can be made at 1, 2, 3, 4, 5, 6, 7, 8, 9, 10 or more days after the agent (e.g., chemotherapeutic agent) is delivered to the subject. A bone marrow sample can be obtained from any portion of bone marrow in the subject's body for this analysis. In order to compare the result to the expected result if no administration was made, data can be collected from one or more control individuals, preferably from several individuals, who receive the same or similar chemotherapy or radiation therapy, but who do not receive IL-1Ra. Preferably, the control population is being treated for the same condition, e.g., for the same type of cancer. An amount is an effective amount (e.g., therapeutically effective amount) if any benefit whatsoever is produced compared to the control population. For example, if the treated individual or group has a bone marrow condition parameter, (e.g., proliferation rate of a given progenitor cell type) whose value, or mean value, is closer to the normal value (e.g., higher than) the value or mean value from a control individual or control group, then the bone marrow condition of the treated individual or group is improved. Statistical methods optionally can be applied to this analysis as appropriate. In different embodiments, an effective amount can be an amount that improves bone marrow condition by at least 5%, at least 10%, at least 15%, at least 20%, at least 25%, at least 30%, at least 40%, at least 50% or more.

Another embodiment in accordance with the invention involves the administration of IL-1Ra as described for the previous embodiment, but with a different measurable outcome. In this embodiment, an effective amount of IL-1Ra results in an increase in peripheral white blood cells. The density (number per unit volume of blood) of white blood cells can be measured by cell counting or by automated methods for determining the number of white blood cells in a sample of whole blood. A blood sample can also be processed to first isolate the white cells prior to counting, or the white cells can be detected using, e.g., labeled antibodies. An effective amount (e.g., therapeutically effective amount) is an amount that produces any increase above a control level either for the total white blood cell population or for any subpopulation thereof.

Another embodiment in accordance with the invention involves the administration of IL-1Ra as described for the previous embodiment, but with a different measurable outcome. In this embodiment, an effective amount of IL-1Ra results in an increase in platelets. The number of platelets can be measured by cell counting or by automated methods for determining the number of platelets in a sample of whole blood. An effective amount (e.g., therapeutically effective amount) is an amount that produces any increase above a control level either for the platelet level in a subject.

IL-1Ra, and Biologically Active Fragments and Variants Thereof

In various embodiments, the methods of the present invention comprise the administration of a IL-1Ra polypeptide to a subject prior to receiving chemotherapy. IL-1Ra is a naturally occurring inhibitor of IL-1 activity, and the molecule has been cloned and expressed in *Escherichia coli* as a recombinant protein. While not wishing to be limited by theory, IL-1Ra has the unique capability of competing with IL-1 for occupancy of IL-1 receptors without being internalized or inducing second signals. IL-1Ra was shown herein to act as an endogenous hematopoietic inhibitor, which was upregulated after 5-FU. The overexpression of endogenous IL-1Ra is responsible for the observed suppression of hematopoiesis after chemotherapy. Thus, IL-1Ra upregulation may be an important protective response that places the bone marrow in a quiescent stage to guard against further insults from chemotherapeutic agents like 5-FU. Therefore, in one embodiment, IL-1Ra is administered before chemotherapy in order to prepare the bone marrow to tolerate the toxic effects of chemotherapy by slowing down the rate of proliferation of bone marrow hematopoietic cells. It was also surprisingly discovered that IL-1Ra administration is effective for increasing thrombopoiesis (i.e., platelet production) following chemotherapy.

Accordingly, increasing platelet levels and bone marrow cells following chemotherapy directly support the use of IL-1Ra as an adjuvant or ancillary therapy before chemotherapy. The survival data further support the use of increased chemotherapy dosages. IL-1Ra is well tolerated clinically and has a short half-life, making it an ideal myeloprotective agent for use in the early post-chemotherapy setting (Chudgar U H et al. *Blood* 1995, 85:2393-2401).

In some embodiments, a subject is administered a biologically active, fragment, domain, variant or homologue of human IL-1Ra. A biologically active fragment, domain, variant, or homologue typically retains the activity of the native protein. These activities include, but are not limited to inhibiting the activity of IL-1 and/or IL-1 receptor. A skilled artisan will be able to identify suitable variants of a polypeptide with well-known techniques. In certain embodiments, one skilled in the art may identify suitable regions of a polypeptide that may be changed without destroying activity by targeting regions not believed to be important for activity. In certain embodiments, one can identify residues and portions of a polypeptide that are conserved among similar polypeptides. In certain embodiments, even areas that may be important for biological activity or for structure may be amenable to conservative amino acid substitutions without destroying the biological activity or without adversely affecting the polypeptide structure. In certain embodiments, the variant if IL-1Ra is a variant having one or more conservative or non-conservative amino acid substitutions. In particular embodiments, the variant may have at least 80%, at least 85%, at least 90%, at least 95%, at least 96%, at least 97%, at least 98%, or at least 99% sequence identity to the IL-1Ra of SEQ ID NO: 1

Additionally, in certain embodiments, one skilled in the art can review structure-function studies and identify residues in similar polypeptides that are important for activity or structure. In view of such a comparison, one can predict the importance of amino acid residues in a protein that correspond to amino acid residues which are important for activity or structure in similar proteins. In certain embodiments, one skilled in the art may opt for chemically similar amino acid substitutions for such predicted important amino acid residues.

In certain embodiments, one skilled in the art can analyze the three-dimensional structure and amino acid sequence in relation to known structures in similar polypeptides. Moreover, in certain embodiments, one skilled in the art may generate test variants containing a single amino acid substitution at each desired amino acid residue. In certain embodiments, the variants can then be screened using activity assays known to those skilled in the art. Such variants could be used to gather information about suitable variants. For example, in certain embodiments, if one discovered that a change to a particular amino acid residue resulted in destroyed, undesirably reduced, or unsuitable activity, variants with such a change may be avoided. In other words, based on information gathered from such routine experiments, one skilled in the art can readily determine the amino acids where further substitutions should be avoided either alone or in combination with other mutations.

Methods of Preparing IL-1Ra Compositions of the Present Invention.

General. The IL-1Ra compositions of the present invention can be produced through the application of recombinant DNA technology. Recombinant polynucleotide constructs encoding a IL-1Ra polypeptide typically include an expression control sequence operably-linked to the coding sequences of IL-1Ra polypeptide, including naturally-associated or heterologous promoter regions. As such, another aspect of the invention includes vectors containing one or more nucleic acid sequences encoding a IL-1Ra polypeptide. For recombinant expression of one or more the polypeptides of the invention, the nucleic acid containing all or a portion of the nucleotide sequence encoding the IL-1Ra polypeptide is inserted into an appropriate cloning vector, or an expression vector (i.e., a vector that contains the necessary elements for the transcription and translation of the inserted polypeptide coding sequence) by recombinant DNA techniques well-known in the art and as detailed below. Methods for producing diverse populations of vectors have been described by Lerner et al., U.S. Pat. Nos. 6,291,160; 6,680,192.

In general, expression vectors useful in recombinant DNA techniques are often in the form of plasmids. In the present specification, "plasmid" and "vector" can be used interchangeably as the plasmid is the most commonly used form of vector. However, the invention is intended to include such other forms of expression vectors that are not technically plasmids, such as viral vectors (e.g., replication defective retroviruses, adenoviruses and adeno-associated viruses), which serve equivalent functions. Such viral vectors permit infection of a subject and expression in that subject of a compound. Preferably, the expression control sequences are eukaryotic promoter systems in vectors capable of transforming or transfecting eukaryotic cells. Once the vector has been incorporated into the appropriate host, the host is maintained under conditions suitable for high level expression of the nucleotide sequences encoding the IL-1Ra polypeptide, and the collection and purification of the IL-1Ra polypeptide. See generally, U.S. Patent Publication No. 20020199213. These expression vectors are typically replicable in the host organisms either as episomes or as an integral part of the host chromosomal DNA. Commonly, expression vectors contain selection markers, e.g., ampicillin-resistance or kanamycin-resistance, to permit detection of those cells transformed with the desired DNA sequences. Vectors can also encode signal peptide, e.g., pectate lyase, useful to direct the secretion of extracellular polypeptides. See U.S. Pat. No. 5,576,195.

The recombinant expression vectors of the invention comprise a nucleic acid encoding a IL-1Ra polypeptide in a form suitable for expression of the nucleic acid in a host cell, which means that the recombinant expression vectors include one or more regulatory sequences, selected on the basis of the host cells to be used for expression that is operably-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, e.g., in Goeddel, *Gene Expression Technology: Methods in Enzymology* 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of polypeptide desired, etc. Typical regulatory sequences useful as promoters of recombinant polypeptide expression (e.g., IL-1Ra polypeptides), include, e.g., but are not limited to, 3-phosphoglycerate kinase and other glycolytic enzymes. Inducible yeast promoters include, among others, promoters from alcohol dehydrogenase, isocytochrome C, and enzymes responsible for maltose and galactose utilization. The expression vectors of the invention can be introduced into host cells to thereby produce polypeptides or peptides, including IL-1Ra polypeptides.

The recombinant expression vectors of the invention can be designed for expression of a IL-1Ra polypeptide in prokaryotic or eukaryotic cells. For example, a IL-1Ra polypeptide can be expressed in bacterial cells such as *Escherichia coli*, insect cells (using baculovirus expression vectors), fungal cells, e.g., yeast, or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, e.g. using T7 promoter regulatory sequences and T7 polymerase.

Expression of polypeptides in prokaryotes is most often carried out in *E. coli* with vectors containing constitutive or inducible promoters directing the expression of either fusion or non-fusion polypeptides. Fusion vectors add a number of amino acids to a polypeptide encoded therein, usually to the amino terminus of the recombinant polypeptide. Such fusion vectors typically serve three purposes: (i) to increase expression of recombinant polypeptide; (ii) to increase the solubility of the recombinant polypeptide; and (iii) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding polypeptide, or polypeptide A, respectively, to the target recombinant polypeptide.

Examples of suitable inducible non-fusion *E. coli* expression vectors include pTrc (Amrann et al., (1988) Gene 69: 301-315), and pET11d (Studier et al., *Gene Expression Technology: Methods in Enzymology* 185, Academic Press, San Diego, Calif. (1990) 60-89). Methods for targeted assembly of distinct active peptide or protein domains to yield multifunctional polypeptides via polypeptide fusion has been described by Pack et al., U.S. Pat. Nos. 6,294,353; 6,692,935. One strategy to maximize recombinant polypeptide expression, e.g., a IL-1Ra polypeptide, in *E. coli* is to express the polypeptide in host bacteria with an impaired capacity to proteolytically cleave the recombinant polypeptide. See, e.g., Gottesman, *Gene Expression Technology: Methods in Enzymology* 185, Academic Press, San Diego, Calif. (1990) 119-128. Another strategy is to alter the nucleic acid sequence of the nucleic acid to be inserted into an expression vector so that the individual codons for each amino acid are those preferentially utilized in the expression host, e.g., *E. coli* (see, e.g., Wada, et al., 1992. Nucl. Acids Res. 20: 2111-2118). Such alteration of nucleic acid sequences of the invention can be carried out by standard DNA synthesis techniques.

In another embodiment, the IL-1Ra polypeptide expression vector is a yeast expression vector. Examples of vectors for expression in yeast *Saccharomyces cerivisae* include pYepSec1 (Baldari, et al., 1987. *EMBO J.* 6: 229-234), pMFa (Kurjan and Herskowitz, *Cell* 30: 933-943, 1982), pJRY88 (Schultz et al., *Gene* 54: 113-123, 1987), pYES2 (Invitrogen Corporation, San Diego, Calif.), and picZ (InVitrogen Corp, San Diego, Calif.). Alternatively, a IL-1Ra polypeptide can be expressed in insect cells using baculovirus expression vectors. Baculovirus vectors available for expression of polypeptides, e.g., IL-1Ra polypeptide, in cultured insect cells (e.g., SF9 cells) include the pAc series (Smith, et al., *Mol. Cell. Biol.* 3: 2156-2165, 1983) and the pVL series (Lucklow and Summers, 1989. *Virology* 170: 31-39).

In yet another embodiment, a nucleic acid encoding a IL-1Ra polypeptide of the invention is expressed in mammalian cells using a mammalian expression vector. Examples of mammalian expression vectors include, e.g., but are not limited to, pCDM8 (Seed, *Nature* 329: 840, 1987) and pMT2PC (Kaufman, et al., *EMBO J.* 6: 187-195, 1987). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells useful for expression of the IL-1Ra polypeptide of the present invention. See, e.g., Chapters 16 and 17 of Sambrook, et al., *Molecular Cloning: A Laboratory Manual*. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., *Genes Dev.* 1: 268-277, 1987), lymphoid-specific promoters (Calame and Eaton, *Adv. Immunol.* 43: 235-275, 1988), in particular promoters of T cell receptors (Winoto and Baltimore, *EMBO J.* 8: 729-733, 1989) and immunoglobulins (Banerji, et al., 1983. *Cell* 33: 729-740; Queen and Baltimore, *Cell* 33: 741-748, 1983.), neuron-specific promoters (e.g., the neurofilament promoter; Byrne and Ruddle, *Proc. Natl. Acad. Sci. USA* 86: 5473-5477, 1989), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, *Science* 249: 374-379, 1990) and the α-fetoprotein promoter (Campes and Tilghman, *Genes Dev.* 3: 537-546, 1989).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation, biolistics or viral-based transfection can be used for other cellular hosts. Other methods used to transform mammalian cells include the use of polybrene, protoplast fusion, liposomes, electroporation, and microinjection (see generally, Sambrook et al., *Molecular Cloning*). Suitable methods for transforming or transfecting host cells can be found in Sambrook, et al., *Molecular Cloning: A Laboratory Manual.*, 2nd ed., Cold Spring Harbor Laboratory, Cold Spring Harbor Laboratory Press, Cold Spring Harbor, N.Y., (1989), and other laboratory manuals. The vectors containing the DNA segments of interest can be transferred into the host cell by well known methods, depending on the type of cellular host.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the IL-1Ra polypeptide or can be introduced on a separate vector. Cells stably transfected with the introduced nucleic acid can be identified by drug selection (e.g., cells that have incorporated the selectable marker gene will survive, while the other cells die).

A host cell that includes an IL-1Ra polypeptide of the present invention, such as a prokaryotic or eukaryotic host cell in culture, can be used to produce (i.e., express) recombinant IL-1Ra polypeptides. In one embodiment, the method comprises culturing the host cell of invention (into which a recombinant expression vector encoding the IL-1Ra polypeptide has been introduced) in a suitable medium such that the IL-1Ra polypeptide is produced. In another embodiment, the method further comprises the step of isolating the IL-1Ra polypeptide from the medium or the host cell. Once expressed, the IL-1Ra polypeptides are purified from culture media and host cells. The IL-1Ra polypeptide can be purified according to standard procedures of the art, including HPLC purification, column chromatography, gel electrophoresis and the like. In one embodiment, the IL-1Ra polypeptide is produced in a host organism by the method of Boss et al., U.S. Pat. No. 4,816,397. Purification of recombinant polypeptides is well known in the art and include ammonium sulfate precipitation, affinity chromatography purification technique, column chromatography, ion exchange purification technique, gel electrophoresis and the like (see generally Scopes, *Protein Purification* (Springer-Verlag, N.Y., 1982).

Other sequences, such as an affinity purification tag (e.g. His Tag), a peptide linker sequence, and the like, can also be included in the IL-1Ra polypeptide of the present invention. In one embodiment, the IL-1Ra polypeptide of the present invention, is fused to a second protein, which can be used as an antigenic tag. Examples of domains that can be fused to polypeptides include not only heterologous signal sequences, but also other heterologous functional regions. The fusion does not necessarily need to be direct, but can occur through linker sequences. Moreover, fusion proteins of the present invention can also be engineered to improve characteristics of the IL-1Ra polypeptide. For instance, a region of additional amino acids, particularly charged amino acids, can be added to the N-terminus of the IL-1Ra polypeptide to improve stability and persistence during purification from the host cell or subsequent handling and storage. Also, peptide moieties can be added to the IL-1Ra polypeptide to facilitate purification. Such regions can be removed prior to final preparation of the IL-1Ra polypeptide. The addition of peptide moieties to facilitate handling of polypeptides are familiar and routine techniques in the art. The IL-1Ra polypeptide of the invention can be fused to marker sequences, such as a peptide which facilitates purification of the fused polypeptide. In preferred embodiments, the marker amino acid sequence is a hexahistidine peptide, such as the tag provided in a pQE vector (QIAGEN, Inc. Chatsworth, Calif.), among others, many of which are commercially available. As described in Gentz et al., *Proc. Natl. Acad. Sci. USA* 86: 821-824, 1989, for instance, hexa-histidine provides for convenient purification of the fusion protein. Another peptide tag useful for purification, the "HA" tag, corresponds to an epitope derived from the influenza hemagglutinin protein. Wilson et al., *Cell* 37: 767, 1984.

Chemotherapeutic Agents

In some embodiments, the methods of the present invention are useful to reduce the hematopoietic toxicity of a chemotherapeutic agent. Chemotherapeutic agents include alkylating agents, antimetabolites, natural products such as plant alkaloids and biologics. Alkylating agents bind covalently to DNA to inhibit DNA synthesis and stop cell growth. Suitable alkylating agents include, but are not limited to, nitrogen mustards such as chlorambucil, cyclophosphamide, estramustine, ifosfamide, mechlorethamine and melphalan, aziridine derivatives such as thiotepa, alkyl sulfonates such as busulfan and nitrosoureas, such as carmustine.

Antimetabolites are agents that block the biosynthesis or use of normal cellular metabolites. Similar to alkylating agents, antimetabolites inhibit DNA synthesis. However, antimetabolites are more effective against slower growing tumors than alkylating agents. Suitable antimetabolites include, but are not limited to, folate analogs such as methotrexate, purine analogs such as fludarabine, mercaptopurine and thioguanine, adenosine analogs such as cladribine and pentostatin and pyrimidine analogs such as capecitabine, cytarabine, depocyt, floxuridine and fluorouracil.

The third class of chemotherapeutic agents are natural products such as antitumor antibiotics. Suitable antitumor antibiotics include, but are not limited to, bleomycin, dactinomycin, daunorubicin, doxorubicin, doxil, epirubicin, idarubicin, mitomycin and mitoxantrone.

Other natural products include the vinca alkaloids which arrest cell division by preventing the formation of the mitotic spindle through disaggregation of microtubules. Suitable vinca alkaloids include, but are not limited to, vincristine, vinblastine, vinorelbine and vindesine. Taxanes are another type of natural product chemotherapeutic agent. Taxanes include, but are not limited to paclitaxel and docetaxel. The taxanes stabilize microtubules to inhibit mitotic spindle assembly to prevent cell division.

Biologics are yet another class of chemotherapeutic agents, and encompass monoclonal antibodies, soluble receptors, protein-chemotherapeutic conjugates, antisense oligonucleotides, and the like. Example of such agents include, Avastin® (bevacizumab), Campath® (alemtuzumab), Erbitux® (cetuximab), Herceptin® (trastuzumab), Rituxan (rituximab), Zevalin™ (ibritumomab tiuxetan), BEXXAR® (Tositumomab and I-131 tositumomab; monoclonal antibody targeting the CD20 antigen and radiolabeled version of the antibody), Mylotarg™ (gemtuzumab ozogamicin).

The chemotherapeutic agents described above can be either cell cycle dependent or cell cycle independent. An agent is cell cycle dependent it its effectiveness depends on which stage of the cell cycle the target (cancer) and non-target (normal) cells are in when the agent is administered. For example, alkylating agents are generally cell cycle dependent, because they are selectively toxic for cells during the S-phase. Cell cycle independent chemotherapeutic agents have approximately equal toxicity at all stages of the cell cycle. An antibody to a tumor antigen, especially if labeled with a toxin or a radioisotope, is likely to be cell cycle independent.

Co-Therapy with Additional Myeolosuppressive Agents

The compositions and methods of the invention can be combined with administration of one or more additional myelosuppressive agents to further prevent damage to bone marrow, or to increase peripheral white blood cells following subsequent chemotherapy or radiotherapy, or to treat cancer or a bone marrow disorder. One such myelosuppressive agent is CCL3, also known as macrophage inflammatory protein-1α. It is understood that in addition to a natural form of CCL3, variants such as fragments, mutants, or chemically modified versions of CCL3 can be used as well, provided that they have a myelosuppressive effect. Agents such as CCL3 block the entry of hematopoietic stem cells into the S-phase of the cell cycle. See, e.g., Clemons et al., *Blood* 92:1532 (1998).

Another example of a myelosuppressive agent is CXCL9. In one embodiment, IL-1Ra is co-administered with CXCL9 prior to the administration of a chemotherapeutic agent. CXCL9 has potent antimyelogenic effects, limiting the proliferation of bone marrow progenitor cells and resulting in a reduction in bone marrow cell number. While not wishing to be limited by any particular mechanism of action, CXCL9 and IL-1Ra are able to inducing a quiescent, nonproliferating state, to prevent destruction of critical progenitor cells or stem cells in bone marrow during chemotherapy or radiotherapy, resulting in improved recovery subsequent to such therapy. Accordingly, the effects of IL-1Ra and CXCL9 can be utilized by a physician to either improve the safety and tolerability of chemotherapy, or to increase the therapeutic efficacy by raising the dose of the chemotherapeutic agent to a level that would not be tolerated without IL-1Ra and CXCL9 treatment.

Administration of CXCL9 (or an agonist of its receptor CXCR3) and IL-1Ra as a therapeutic agent prior to administration of a chemotherapy agent results in more rapid recovery of bone marrow and circulating leukocytes as well as a higher survival rate in animals. Administration of CXCL9 refers to administering a CXCL9 polypeptide, including sequence variants such as insertions, deletions, and conservative amino acid substitutions, or related forms such as mutations or CXCL9 polypeptides of related species having a high degree of sequence similarity. The term "CXCR3 agonist" refers to substances that bind CXCR3 and promote the activity of CXCR3, in particular the activity produced in a cell when CXCL9 binds to and activates CXCR3. CXCR3 agonists include natural ligands for CXCR such as IP-10, Mig, I-TAC, and BCA-1 (as well as biologically active fragments and modifications thereof), and also includes both known and novel compounds that possess agonistic activity with respect to CXCR3. Exemplary agonists of CXCR3 are generally described in U.S. Pat. No. 6,184,358, WO 2005/113597, WO 2004/083394, and U.S. Publication NO. 2005/0119174.

The term "CXCR3 antagonist" includes substances that bind to CXCR3 but do not promote the activity of CXCR3 in a cell, and may block or inhibit the activity of CXCR3, either acting alone or in the presence of a natural ligand or agonist of CXCR3, and also includes substances that bind to a natural ligand of CXCR3 and prevent it from binding to CXCR3 or activating CXCR3. CXCR3 antagonists can be neutral antagonists, for example, which block the activity of CXCR3 by inhibiting the binding of physiological ligands to CXCR3, or inverse agonists, which shift the equilibrium of the active form and inactive form of CXCR3 toward the more inactive form. CXCR3 antagonists encompass both known and novel compounds that possess any one of the above-described properties. Examples of CXCR3 antagonists include degradation products of physiological ligands for CXCR3 such as IP-10, Mig, I-TAC, and BCA-1; certain kinds of CC chemokines that possess affinity for CXCR3, such as eotaxin (*J. Biol. Chem.*, 273(29): 18288-18291 (1998)). Further exemplary antagonists of CXCR3, including small molecule agonists, are generally described in International Publication Nos. WO 2006/088920, WO 2006/088837, WO 2006/091428, WO 2006/088921, WO 2006/088919, WO 2006/088836, WO 2007/002742, WO 2007/002701, WO 2006/137934, WO 2006/129679, WO 2005/113597, WO 2002/085861, U.S. Publication Nos. 2006/0240437, 2006/0204498, 2006/0276480, 2006/0276479, 2006/0276448, 2006/0276457, 2006/0217392, 2007/0021611, 2007/0015773, 2005/0119174, 2004/0242498, 2003/0077247, 2002/0018776, 2002/0169159 and European Publication Nos. EP 1603896, EP 1723970.

The amino acid sequences of IP-10, Mig, I-TAC and BCA-1, which are physiological ligands for CXCR3, and the nucleotide sequences of their genes are known. For example, the human cDNA sequences of these ligands have been registered with GenBank under accession numbers NM 001565, NM 002416, NM 005409, and NM 006419, respectively. In the present invention, "IP-10", "Mig", "I-TAC", and "BCA-1" encompass, in addition to the corresponding naturally occurring chemokine proteins derived from humans and other mammals, recombinant proteins produced from recombinant cells containing DNAs that encode them.

CXCR3 agonists or antagonists can also be used in the form of a prodrug that is metabolized in the body of a recipient animal and results in a substance that exhibits the respective agonist or antagonist activity with respect to CXCR3. When the CXCR3 agonist or antagonist is a peptide substance such as IP-10, Mig, I-TAC or BCA-1, "prodrugs" thereof also encompass an expression vector containing a nucleic acid sequence that encodes the peptide, and a host cell transfected with such an expression vector. In the expression vector, a DNA that encodes a physiological ligand possessing agonist or antagonist activity against CXCR3, such as IP-10, Mig, I-TAC or BCA-1, or a modification thereof, is operably linked to a promoter capable of exhibiting promoter activity in the cells of the recipient mammal.

In one embodiment, IL-1Ra and CXCL9 are administered as part of a therapeutic protocol involving chemotherapy used to treat cancer. Co-administration refers to administration of a first amount of IL-1Ra and a second amount of CXCL9 (or an agonist of CXCR3). Coadministration encompasses administration of the amounts of the compounds in an essentially simultaneous manner, such as a single pharmaceutical composition or a fusion polypeptide. In addition, such co-administration also encompasses use of each compound in a sequential manner in either order. When coadministration involves the separate administration of the first amount of IL-1Ra and a second amount of CXCL9, the compounds are administered sufficiently close in time to have the desired therapeutic effect. For example, the period of time between each administration which can result in the desired therapeutic effect, can range from minutes to hours to days, and can be determined taking into account the properties of each compound such as potency, solubility, bioavailability, plasma half-life and kinetic profile. In a particular embodiment, IL-1Ra and CXCL9 are administered simultaneously from about 1-10 days, preferably about 2-5 days before chemotherapy.

In a further embodiment, preventive administration of IL-1Ra and CXCL9 (or a CXCR3 agonist) before chemotherapy or radiotherapy is supplemented with an effective amount of the post-chemotherapy or post-radiotherapy administration of an agent that is antagonistic to CXCL9 activity. Such agents include, but are not limited to, an antagonistic antibody to CXCL9, an siRNA or antisense nucleic acid specific for CXCL9 expression, an antagonistic antibody to CXCR3 (the natural receptor for the CXCL9 ligand), an siRNA or antisense nucleic acid specific for CXCR3 expression, and an antagonist of CXCR3 function (e.g., a small molecule antagonist). Any of these antagonists of CXCL9 or combinations thereof can be used according to the invention. For human subjects, administration of a fully human antibody to human CXCL9 is especially preferred.

The time course of administration can vary, but it is generally beneficial to adjust it to coincide with the time course of the increased expression of CXCL9 following chemotherapy or radiotherapy. That is, for example, if the subject's CXCL9 expression is expected to peak at about 7 days following chemotherapy, then a CXCL9 antagonistic agent can be administered so as to be present in a therapeutically effective amount by day 7, and optionally for one or more days before and after day 7. The CXCL9 antagonistic agent can be delivered in a single dose or in multiple doses, e.g., in daily doses. The agent can be administered, e.g., only on day 0 (the day of chemotherapy or radiotherapy, or exposure to a bone marrow damaging agent), or on one or more subsequent days, such as on days 0, 1, 2, 3, 4, 5, 6, 7, 8, 9, 10, and later, or on any combination of those days. The agent can also be administered every other day, or can be administered as a long acting conjugate, such as a PEGylated antibody.

In variants of this embodiment, different endpoints can be used to determine an effective dose. As for earlier embodiments, one possible endpoint is an increase in bone marrow cell density compared to a control group who does not receive the CXCL9 antagonistic agent. Another possible endpoint is an increase in peripheral white blood cells. A third endpoint is efficacy in treating cancer, wherein an improvement in either safety or effectiveness of the accompanying cancer therapy, i.e., chemotherapy or radiation therapy, is observed compared to a control group.

In yet other embodiments in accordance with the invention, no CXCL9 or CXCR3 agonist is administered prior to the treatment with a chemotherapy agent or radiation, but after the therapy is performed, an effective amount of a CXCL9 antagonistic agent is administered to the subject. The same factors apply as for the previous embodiments with respect to the type of subject, the time course of administering the agent, the type of agent (i.e., an antagonistic antibody to CXCL9, an siRNA or antisense nucleic acid specific for CXCL9, an antagonistic antibody to CXCR3, an siRNA or antisense nucleic acid specific for CXCR3, or an antagonist of CXCR3), and the type of endpoint for determining an effective amount.

In one aspect, a method of the invention can comprise administering an agent selected from an anti-CXCL9 antibody, a CXCL9 siRNA, a CXCL9 antisense nucleic acid, a CXCR3 antibody, a CXCR3 antisense nucleic acid, a CXCR3 siRNA and combinations thereof. For example, the agent can be administered in daily doses for, but not limited to, two or more days following the administration of chemotherapy or said radiotherapy. Preferably, the agent can be administered for at least 10 days following the administration of chemotherapy or radiotherapy. In another aspect of the invention, an anti-CXCL9 antibody or CXCR3 antibody can be a polyclonal antibody or a monoclonal antibody. The anti-CXCL9 antibody or CXCR3 antibody can also be a Fab fragment, a scFv antibody or a single domain antibody. The anti-CXCL9 antibody or CXCR3 antibody can also be a chimeric antibody, a humanized antibody (optionally including back mutations) or a human antibody. An anti-CXCL9 antibody or CXCR3 antibody of the invention can also be provided as a conjugated form. Preferably, the effective amount of the anti-CXCL9 antibody or CXCR3 antibody increases bone marrow cell density for the subject.

In one aspect, a method of the invention comprises administering CXCL9 siRNA. For example, CXCL9 siRNA can comprise a sequence complementary to 18 to 30 consecutive nucleotides of the CXCL9 coding sequence or CXCR3 siRNA can comprise a sequence complementary to 18 to 30 consecutive nucleotides of the CXCR3 coding sequence. Preferably, the effective amount of the siRNA increases bone marrow cell density for the subject.

Co-Therapy with Hematopoietic Growth Factors

The compositions and methods of the invention can also be administered together with the administration of a hematopoietic growth factor following chemotherapy or radiotherapy. The hematopoietic growth factor can be a naturally occurring molecule or a fragment, mutant, or chemical modification thereof, provided that the growth factor is effective in either stimulating the proliferation of one or more types of bone marrow stem cell or progenitor cell or promoting the differentiation and development of a stem cell or progenitor cell leading to myelogenesis or hematopoiesis. Examples of hematopoietic growth factors include stem cell factor (SCF), interleukin 3 (IL-3), interleukin 6 (IL-6), granulocyte-colony stimulating factor (G-CSF) and macrophage-colony stimulating factor (M-CSF). Increased levels of hematopoietic growth factors (HGFs) induce mobilization and proliferation of hematopoietic cells.

Radiation Therapy

In one embodiment, the IL-1Ra treatment is administered with chemotherapy and/or radiation therapy. Radiation therapy (radiotherapy) can be used to treat almost every type of solid tumor, including brain, breast, cervix, larynx, lung, pancreas, prostate, skin, spine, stomach, uterus cancers, or soft tissue sarcomas. The appropriate dosage of radiation depends on a number of factors, including the type of cancer, type of radiation treatment, as well as proximity of radiation therapy to tissues and organs nearby that may be damaged by radiation, and tolerances of those tissues and organs to radiation. For example, radiation doses range from a low of 65 Gy to a high of 81 Gy for the treatment of prostate cancer, while for the treatment of solid epithelial tumors, the dosage can range between 50 Gy and 70 Gy. In contrast, lymphomas typically receive lower doses, ranging between 20 to 40 Gy in daily doses.

Radiation therapies which are suitable for use in the combination treatments described herein, include the use of a) external beam radiation; and b) a radiopharmaceutical agent which comprises a radiation-emitting radioisotope.

External beam radiation therapy for the treatment of cancer uses a radiation source that is external to the patient, typically either a radioisotope, such as $^{60}$Co, $^{137}$Cs or a high energy x-ray source, such as a linear accelerator. The external source produces a collimated beam directed into the patient to the tumor site. External-source radiation therapy avoids some of the problems of internal-source radiation therapy, but it undesirably and necessarily irradiates a significant volume of non-tumorous or healthy tissue in the path of the radiation beam along with the tumorous tissue.

The adverse effect of irradiating of healthy tissue can be reduced, while maintaining a given dose of radiation in the tumorous tissue, by projecting the external radiation beam into the patient at a variety of "gantry" angles with the beams converging on the tumor site. The particular volume elements of healthy tissue, along the path of the radiation beam, change, reducing the total dose to each such element of healthy tissue during the entire treatment.

The irradiation of healthy tissue also can be reduced by tightly collimating the radiation beam to the general cross section of the tumor taken perpendicular to the axis of the radiation beam. Numerous systems exist for producing such a circumferential collimation, some of which use multiple sliding shutters which, piecewise, can generate a radio-opaque mask of arbitrary outline.

A new method of external radiotherapy, called conformal radiotherapy or three-dimensional conformal radiotherapy, can also be used to treat tumors that, in the past, were considered too close to a vital organ or tissue to permit effective radiotherapy. The complex process of conformal radiotherapy begins with the creation of a three-dimensional reconstruction of a patient's tumors and normal adjacent anatomy. The 3-D computer images thus developed are used to deliver highly focused, or "conformed" radiotherapy to the tumor while sparing normal adjacent tissue, resulting in overall higher dosage of radiation than previously permitted, while causing less harm to proximal tissues and organs.

A "radiopharmaceutical agent", as defined herein, refers to a pharmaceutical agent which contains at least one radiation-emitting radioisotope. Radiopharmaceutical agents are routinely used in nuclear medicine for the diagnosis and/or therapy of various diseases. The radiolabeled pharmaceutical agent, for example, a radiolabeled antibody, contains a radioisotope (RI) which serves as the radiation source. As contemplated herein, the term "radioisotope" includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

As used herein, a "metallic radioisotope" is any suitable metallic radioisotope useful in a therapeutic or diagnostic procedure in vivo or in vitro. Suitable metallic radioisotopes include, but are not limited to: Actinium-225, Antimony-124, Antimony-125, Arsenic-74, Barium-103, Barium-140, Beryllium-7, Bismuth-206, Bismuth-207, Bismuth212, Bismuth213, Cadmium-109, Cadmium-15m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-60, Copper-62, Copper-64, Copper-67, Erbium-169, Europium-152, Gallium-64, Gallium-67, Gallium-68, Gadolinium153, Gadolinium-157 Gold-195, Gold-199, Hafnium-175, Hafnium-175-181, Holmium-166, Indium-110, Indium-111, Iridium-192, Iron 55, Iron-59, Krypton85, Lead-203, Lead-210, Lutetium-177, Manganese-54, Mercury-197, Mercury203, Molybdenum-99, Neodymium-147, Neptunium-237, Nickel-63, Niobium-95, Osmium-185+191, Palladium-103, Palladium-109, Platinum-195m, Praseodymium-143, Promethium-147, Promethium-149, Protactinium-233, Radium-226, Rhenium-186, Rhenium-188, Rubidium-86, Ruthenium-97, Ruthenium-103, Ruthenium-105, Ruthenium-106, Samarium-153, Scandium-44, Scandium-46, Scandium-47, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, Zirconium-89, and Zirconium-95.

As used herein, a "non-metallic radioisotope" is any suitable nonmetallic radioisotope (non-metallic radioisotope) useful in a therapeutic or diagnostic procedure in vivo or in vitro. Suitable non-metallic radioisotopes include, but are not limited to: Iodine-131, Iodine-125, Iodine-123, Phosphorus-32, Astatine-211, Fluorine-18, Carbon-11, Oxygen-15, Bromine-76, and Nitrogen-13.

Identifying the most appropriate isotope for radiotherapy requires weighing a variety of factors. These include tumor uptake and retention, blood clearance, rate of radiation delivery, half-life and specific activity of the radioisotope, and the feasibility of large-scale production of the radioisotope in an economical fashion. The key point for a therapeutic radiopharmaceutical is to deliver the requisite amount of radiation dose to the tumor cells and to achieve a cytotoxic or tumoricidal effect while not causing unmanageable side-effects.

It is preferred that the physical half-life of the therapeutic radioisotope be similar to the biological half-life of the radiopharmaceutical at the tumor site. For example, if the half-life of the radioisotope is too short, much of the decay will have occurred before the radiopharmaceutical has reached maximum target/background ratio. On the other hand, too long a half-life would cause unnecessary radiation dose to normal tissues. Ideally, the radioisotope should have a long enough half-life to attain a minimum dose rate and to irradiate all the cells during the most radiation sensitive phases of the cell cycle. In addition, the half-life of a radioisotope has to be long enough to allow adequate time for manufacturing, release, and transportation.

Other practical considerations in selecting a radioisotope for a given application in tumor therapy are availability and quality. The purity has to be sufficient and reproducible, as trace amounts of impurities can affect the radiolabeling and radiochemical purity of the radiopharmaceutical.

The target receptor sites in tumors are typically limited in number. As such it is preferred that the radioisotope have high specific activity. The specific activity depends primarily on the production method. Trace metal contaminants must be minimized as they often compete with the radioisotope for the chelator and their metal complexes compete for receptor binding with the radiolabeled chelated agent.

The type of radiation that is suitable for use in the methods of the present invention can vary. For example, radiation can be electromagnetic or particulate in nature. Electromagnetic radiation useful in the practice of this invention includes, but is not limited to, x-rays and gamma rays. Particulate radiation useful in the practice of this invention includes, but is not limited to, electron beams (beta particles), protons beams, neutron beams, alpha particles, and negative pi mesons. The radiation can be delivered using conventional radiological treatment apparatus and methods, and by intraoperative and stereotactic methods. Additional discussion regarding radiation treatments suitable for use in the practice of this invention can be found throughout Steven A. Leibel et al., *Textbook of Radiation Oncology* (1998) (W.B. Saunders Company), and particularly in Chapters 13 and 14. Radiation can also be delivered by other methods such as targeted delivery, for example by radioactive "seeds," or by systemic delivery of targeted radioactive conjugates. J. Padawer et al., Combined Treatment with Radioestradiol lucanthone in Mouse C3HBA Mammary Adenocarcinoma and with Estradiol lucanthone in an Estrogen Bioassay, *Int. J. Radiat. Oncol. Biol. Phys.* 7:347-357 (1981). Other radiation delivery methods can be used in the practice of this invention.

For tumor therapy, both α and β-particle emitters have been investigated. Alpha particles are particularly good cytotoxic agents because they dissipate a large amount of energy within one or two cell diameters. The β-particle emitters have relatively long penetration range (2-12 mm in the tissue) depending on the energy level. The long-range penetration is particularly important for solid tumors that have heterogeneous blood flow and/or receptor expression. The β-particle emitters yield a more homogeneous dose distribution even when they are heterogeneously distributed within the target tissue.

Dosage and Formulation of Pharmaceutical Compositions

The present invention envisions treating a disease or condition, for example, cancer, in a subject by the administration of IL-1Ra compositions in conjunction with chemotherapy. Administration of the IL-1Ra compositions in accordance with the present invention may be continuous or intermittent, depending, for example, upon the recipient's physiological condition, whether the purpose of the administration is therapeutic or prophylactic, and other factors known to skilled practitioners. The administration of the vaccines of the invention may be essentially continuous over a preselected period of time or may be in a series of spaced doses. Both local and systemic administration is contemplated.

In one embodiment, the IL-1Ra polypeptides are administered directly to a subject to achieve the desired response. The amount administered will vary depending on various factors including, but not limited to, the composition chosen, the particular disease, the weight, the physical condition, and the age of the subject, and whether prevention or treatment is to be achieved. Such factors can be readily determined by the clinician employing animal models or other test systems which are well known to the art.

Typically, an effective amount of the compositions of the present invention, sufficient for achieving a therapeutic or prophylactic effect, range from about 0.000001 mg per kilogram body weight per day to about 10,000 mg per kilogram body weight per day. Preferably, the dosage ranges are from about 0.0001 mg per kilogram body weight per day to about 100 mg per kilogram body weight per day. For administration of IL-1Ra polypeptides, the dosage ranges from about 0.0001 to 100 mg/kg, and more usually 0.01 to 5 mg/kg every day, every two days or every three days. For example dosages can be 0.1 mg/kg body weight or 1 mg/kg body weight every day, every two days or every three days or within the range of 1-10 mg/kg every day, every two days or every three days.

Toxicity. Preferably, an effective amount (e.g., dose) of IL-1Ra polypeptides described herein will provide therapeutic benefit without causing substantial toxicity to the subject. Toxicity of the IL-1Ra polypeptides described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the IL-1Ra polypeptides described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the subject's condition. See, e.g., Fingl et al., In: *The Pharmacological Basis of Therapeutics*, Ch. 1 (1975).

One or more suitable unit dosage forms having the IL-1Ra polypeptides of the invention, which, as discussed below, may optionally be formulated for sustained release (for example using microencapsulation, see WO 94/07529, and U.S. Pat. No. 4,962,091), can be administered by a variety of routes including parenteral, including by intravenous and intramuscular routes. For example, the vaccine may be directly injected into a tumor. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the vaccine compositions of the invention are prepared for administration, they are preferably combined with a pharmaceutically acceptable carrier, diluent or excipient to form a pharmaceutical formulation, or unit dosage form. The total active ingredients in such formulations include from 0.1 to 99.9% by weight of the formulation. A "pharmaceutically acceptable carrier" is a carrier, diluent, excipient, and/or salt that is compatible with the other ingredients of the formulation, and not deleterious to the recipient thereof. The active ingredient for administration may be present as a powder or as granules; as a solution, a suspension or an emulsion.

Pharmaceutical formulations containing the therapeutic agents of the invention can be prepared by procedures known in the art using well-known and readily available ingredients. The therapeutic agents of the invention can also be formulated as solutions appropriate for parenteral administration, for instance by intramuscular, subcutaneous or intravenous routes. The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

It will be appreciated that the unit content of active ingredient or ingredients contained in an individual aerosol dose of each dosage form need not in itself constitute an effective amount for treating the particular indication or disease since the necessary effective amount can be reached by administration of a plurality of dosage units. Moreover, the effective amount may be achieved using less than the dose in the dosage form, either individually, or in a series of administrations.

The pharmaceutical formulations of the present invention may include, as optional ingredients, pharmaceutically acceptable carriers, diluents, solubilizing or emulsifying agents, and salts of the type that are well-known in the art. Specific non-limiting examples of the carriers and/or diluents that are useful in the pharmaceutical formulations of the present invention include water and physiologically acceptable buffered saline solutions, such as phosphate buffered saline solutions pH 7.0-8.0.

In general, water, suitable oil, saline, aqueous dextrose (glucose), and related sugar solutions and glycols such as propylene glycol or polyethylene glycols are suitable carriers for parenteral solutions. Solutions for parenteral administration contain the active ingredient, suitable stabilizing agents and, if necessary, buffer substances. Antioxidizing agents such as sodium bisulfate, sodium sulfite or ascorbic acid, either alone or combined, are suitable stabilizing agents. Also used are citric acid and its salts and sodium ethylenediaminetetraacetic acid (EDTA). In addition, parenteral solutions can contain preservatives such as benzalkonium chloride, methyl- or propyl-paraben and chlorobutanol. Suitable pharmaceutical carriers are described in *Remington's Pharmaceutical Sciences*, a standard reference text in this field.

Additionally, standard pharmaceutical methods can be employed to control the duration of action. These are well known in the art and include control release preparations and can include appropriate macromolecules, for example polymers, polyesters, polyamino acids, polyvinyl, pyrolidone, ethylenevinylacetate, methyl cellulose, carboxymethyl cellulose or protamine sulfate. The concentration of macromolecules as well as the methods of incorporation can be adjusted in order to control release. Additionally, the agent can be incorporated into particles of polymeric materials such as polyesters, polyamino acids, hydrogels, poly(lactic acid) or ethylenevinylacetate copolymers. In addition to being incorporated, these agents can also be used to trap the compound in microcapsules.

Accordingly, the pharmaceutical composition of the present invention may be delivered via various routes and to various sites in an mammal body to achieve a particular effect. One skilled in the art will recognize that although more than one route can be used for administration, a particular route can provide a more immediate and more effective reaction than another route. Local or systemic delivery can be accomplished by administration comprising application or instillation of the formulation into body cavities, inhalation or insufflation of an aerosol, or by parenteral introduction, comprising intramuscular, intravenous, peritoneal, subcutaneous, intradermal, as well as topical administration.

The active ingredients of the present invention can be provided in unit dosage form wherein each dosage unit, e.g., a teaspoonful, tablet, solution, or suppository, contains a predetermined amount of the composition, alone or in appropriate combination with other active agents. The term "unit dosage form" as used herein refers to physically discrete units suitable as unitary dosages for human and mammal subjects, each unit containing a predetermined quantity of the compositions of the present invention, alone or in combination with other active agents, calculated in an amount sufficient to produce the desired effect, in association with a pharmaceutically acceptable diluent, carrier, or vehicle, where appropriate. The specifications for the unit dosage forms of the present invention depend on the particular effect to be achieved and the particular pharmacodynamics associated with the pharmaceutical composition in the particular subject.

Formulations of Pharmaceutical Compositions. According to the methods of the present invention, the IL-1Ra polypeptides can be incorporated into pharmaceutical compositions suitable for administration. The pharmaceutical compositions generally comprise recombinant or substantially purified IL-1Ra polypeptides and a pharmaceutically-acceptable carrier in a form suitable for administration to a subject. Pharmaceutically-acceptable carriers are determined in part by the particular composition being administered, as well as by the particular method used to administer the composition. Accordingly, there is a wide variety of suitable formulations of pharmaceutical compositions for administering the antibody compositions (see, e.g., *Remington's Pharmaceutical Sciences*, Mack Publishing Co., Easton, Pa. 18$^{th}$ ed., 1990). The pharmaceutical compositions are generally formulated as sterile, substantially isotonic and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, diluents and reagents, are used interchangeably and represent that the materials are capable of administration to or upon a subject without the production of undesirable physiological effects to a degree that would prohibit administration of the composition. For example, "pharmaceutically-acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. "Pharmaceutically-acceptable salts and esters" means salts and esters that are pharmaceutically-acceptable and have the desired pharmacological properties. Such salts include salts that can be formed where acidic protons present in the IL-1Ra polypeptides are capable of reacting with inorganic or organic bases. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically-acceptable esters include esters formed from carboxy, sulfonyloxy, and phosphonoxy groups present in the IL-1Ra polypeptide, e.g., $C_{1-6}$ alkyl esters. When there are two acidic groups present, a pharmaceutically-acceptable salt or ester can be a mono-acid-mono-salt or ester or a di-salt or ester; and similarly where there are more than two acidic groups present, some or all of such groups can be salified or esterified. The IL-1Ra polypeptides named in this invention can be present in unsalified or unesterified form, or in salified and/or esterified form, and the naming of such IL-1Ra polypeptide is intended to include both the original (unsalified and unesterified) compound and its pharmaceutically-acceptable salts and esters. Also, certain IL-1Ra polypeptides named in this invention can be present in more than one stereoisomeric form, and the naming of such IL-1Ra polypeptides is intended to include all single stereoisomers and all mixtures (whether racemic or otherwise) of such stereoisomers. A person of ordinary skill in the art, would have no difficulty determining the appropriate timing, sequence and dosages of administration for particular drugs and compositions of the present invention.

Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and compounds for pharmaceutically active substances is well known in the art. Except insofar as any conventional media or compound is incompatible with the IL-1Ra polypeptides, use thereof in the compositions is contemplated. Supplementary active compounds can also be incorporated into the compositions.

A pharmaceutical composition of the invention is formulated to be compatible with its intended route of administration. The IL-1Ra polypeptides compositions of the present invention can be administered by parenteral, topical, intravenous, oral, subcutaneous, intraarterial, intradermal, transdermal, rectal, intracranial, intraperitoneal, intranasal; intramuscular route or as inhalants. The IL-1Ra polypeptides can optionally be administered in combination with other agents that are at least partly effective in treating various diseases including various actin- or microfilament-related diseases.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as mannitol, sorbitol, sodium chloride in the composition. Prolonged absorption of the injectable compositions can be brought about by including in the composition a compound which delays absorption, e.g., aluminum monostearate and gelatin.

Sterile injectable solutions can be prepared by incorporating the IL-1Ra polypeptides in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. The agents of this invention can be administered in the form of a depot injection or implant preparation which can be formulated in such a manner as to permit a sustained or pulsatile release of the active ingredient.

Oral compositions generally include an inert diluent or an edible carrier. They can be enclosed in gelatin capsules or compressed into tablets. For the purpose of oral therapeutic administration, the binding agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel, or corn starch; a lubricant such as magnesium stearate or Sterotes; a glidant such as colloidal silicon dioxide; a sweetening compound such as sucrose or saccharin; or a flavoring compound such as peppermint, methyl salicylate, or orange flavoring.

For administration by inhalation, the IL-1Ra polypeptides are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the IL-1Ra polypeptides is formulated into ointments, salves, gels, or creams as generally known in the art.

The IL-1Ra polypeptides can also be prepared as pharmaceutical compositions in the form of suppositories (e.g., with conventional suppository bases such as cocoa butter and other glycerides) or retention enemas for rectal delivery.

In one embodiment, the IL-1Ra polypeptide is prepared with carriers that will protect the IL-1Ra polypeptide against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically-acceptable carriers. These can be prepared according to methods known to those skilled in the art, e.g., as described in U.S. Pat. No. 4,522,811.

Experimental Animal Models

The methods and compositions of the invention have beneficial effects on myelogenesis. Various models exist, both in vivo (in animals and humans) and in vitro, that allow certain aspects of the process of myelogenesis to be investigated. Such models can be used to study the effectiveness of the compositions and methods of the invention, and, for example, to select a dosage or administration protocol. For example, the level or proliferative activity of bone marrow stem cells or bone marrow progenitor cells can be determined either in bone marrow or in circulating blood. Progenitor cells can be isolated from mice or humans, their numbers counted, and the cells cultured to ascertain the effectiveness of a composition or method of the invention in stimulating bone marrow regeneration of the progenitor cell donor. Alternatively, a competitive regeneration assay can be performed, in which the repopulating ability of a test marrow specimen is evaluated in lethally irradiated mice. In vitro colony assays, such as the CFU-GM, BFU-E, CFU-GEMM, and CFu-Blast assays, also can be employed to measure the number of healthy stem cells in a sample from a treated animal or human. Further examples of such assays can be found in Mauch et al., $Int.\ J.\ Radiation$ 31:1319-1339 (1995).

One aspect of the invention is a method for treating cancer. One such method includes administering to a cancer patient a IL1-Ra prior to administering chemotherapy or radiation therapy. Another such method includes administering IL-1Ra after administering chemotherapy or radiation therapy. A number of animal models of cancer are known which can be used to select an appropriate dose or administration protocol for carrying out a method or using a composition of the invention.

Colon adenocarcinoma in rodents induced by the procarcinogen 1,2-dimethylhydrazine and its metabolite azoxymethane (AOM) is a well-characterized carcinogen-induced tumor because of its morphological similarity to human colon cancer, high reproducibility and relatively short latency period (Shamsuddin, (1986) $Human\ Path.$ 17:451-453). This rodent tumor model is similar to human colon adenocarcinoma not only in its morphology (Shamsuddin & Trump, (1981) $J.\ Natl.\ Cancer\ Inst.$ 66:389-401) but also in the genes that are involved in tumorigenesis (Shivapurkar et al., (1995) $Cancer\ Lett.$ 96:63-70; Takahashi et al., (2000) $Carcinogenesis$ 21:1117-1120).

In addition to chemical carcinogen-induced models of colon cancer in rodents, gene disruption of the catalytic subunits of phosphoinositide-3-OH kinase (PI3-Kγ) (Sasaki et al., (2000) $Nature$ 406:897-902) or the guanosine-binding protein Gαi2 (Rudolph et al., (1995) $Nat.\ Genet.$ 10: 143-50) causes spontaneous colon cancer in rodents. These studies indicate that potential causes other than alterations in the prototypical tumor suppressor genes and oncogenes could be involved in the etiology of human colon cancer.

A number of animal models for oral squamous cell carcinoma have been developed, including rat, mouse and hamster models. A hamster cheek pouch tumor model induced by the carcinogen 7,12-dimethylbenzanthracene remains one of the most common models (Baker (1986) Malignant neoplasms of the oral cavity. In: $Otolaryngology—Head\ and\ Neck\ Surgery$, Cummings et al. (eds.) pp. 1281-1343. St. Louis, Mo.: CV Mosby), but exhibits a number of differences from human oral cavity tumorigenesis. A recent mouse model using the carcinogen 4-nitroquinoline 1-oxide (4-NQO) has been developed which more closely simulates many aspects of human oral cavity and esophageal carcinogenesis (Tang et al. (2004) $Clin.\ Cancer\ Res.$ 10: 301-313).

An animal model for multiple myeloma has been described (Garrett et al. (1997) $Bone$ 20: 515-520), which uses a murine myeloma cell line 5TGM1 that causes lesions characteristic of human myeloma when injected into mice. Such lesions include severe osteolysis and the involvement of non-bone organs including liver and kidney. Mice inoculated with cultured 5TGM1 cells predictably and reproducibly develop disease, symptoms of which include the formation of a monoclonal gammopathy and radiologic bone lesions.

A number of animal models for the study of glioma exist, including an intracerebral rat glioma model (Sandstrom et al. (2004) $Br.\ J.\ Cancer,$ 91: 1174-1180), and a murine model using injection of dog-derived J3T1 glioma cells (U.S. Pat. No. 6,677,155).

Animal models for the study of non-small cell lung cancer have been previously described, for example, by xenografting human tumors by subcutaneous transplantation of LC-6 human non-small cell lung cancer into BALB/C-nu/nu mice (Tashiro et al. (1989) $Cancer\ Chemother.\ Pharmacol.$ 24, 187).

An animal model for the study of stomach cancer has been described which uses AZ-521 human stomach cancer xenografts in nude mice (Fukushima et. al. (2000) $Biochem.\ Pharmacol.$ 59, 1227-1236).

Numerous animal models of AML have been previously described, including in rats (Blatt, J et al. (1991) *Leuk. Res.* 15:391-394), and SCID mice (Vey, N. et al. (2000) *Clin. Cancer Res.,* 6:731-736).

A number of animal models used for the study of HCC have been described (Chisari et al., (1985) *Science* 230: 1157-1160; Babinet et al. (1985) *Science* 230: 1160-11; U.S. Publication No. 2004/0016011). These references disclose the generation of transgenic mouse models of HCC by incorporating the HBV virus into the genome.

Animal models with experimental metastasis pattern resembling those frequently observed in human patients (Engebraaten & Fodstad, (1999) *Int. J. Cancer.* 82:219-25), which use MA-11 and MT-1, two estrogen and progesterone receptor-negative human breast cancer cell lines. Other models for breast cancer include U.S. Publication No. 2003/0215861 (herein incorporated by reference). Alternatively, the ability of the compounds of the present invention to function as anti-breast cancer agents, either alone or in combination with other agents, can be demonstrated in vivo in carcinogen induced mammary tumors in wild type Sprague-Dawley Rats (Thompson H. J et al, *Carcinogenesis,* (1992) 13:1535-1539).

A number of animal models for ovarian cancer are known in the art. For example, Connolly et al. ((2003) *Cancer Research,* 63, 1389-1397), discloses methods of developing epithelial ovarian cancer in mice by chimeric expression of the SV40 Tag under control of the MISIIR promoter. In another example, Liu et al. (*Cancer Research* 64, 1655-1663 (2004)) have introduced human HRAS or KRAS oncogenes into immortalized human ovarian surface epithelial cells, which form subcutaneous tumors after injection into immunocompromised mice.

Numerous animal models for the study of prostate cancer are available. One murine model, using prostate cancer xenografts introduced into SCID mice, is disclosed in U.S. Pat. No. 6,756,036. Alternatively, an orthotopic mouse model of metastatic prostate cancer can be used, as disclosed in U.S. Publication No. 2004/0009508.

All publications, patent applications, issued patents, and other documents referred to in the present disclosure are herein incorporated by reference as if each individual publication, patent application, issued patent, or other document were specifically and individually indicated to be incorporated by reference in its entirety. Definitions that are contained in text incorporated by reference are excluded to the extent that they contradict definitions in this disclosure.

EXAMPLES

The present invention is further illustrated by the following examples, which should not be construed as limiting in any way.

Example 1

Methods for Analyzing In Vivo Myeloprotective Effects of IL-1Ra in Mice

The therapeutic utility of rMuIL-1Ra in enhancing hematopoietic recovery was investigated in mice according to the procedures set forth in this Example. Using the methods described below, it would also be possible for the skilled artisan to generate and/or compare additional IL-1Ra polypeptides to the ones shown in these examples.

1. Mice and Sample Handling

Specific pathogen-free BALB/c male mice, at 8 weeks old, were purchased from Shanghai Laboratory Animal Center and quarantined for at least 7 days prior to use. Mice were maintained on commercial rodent food, given sterile water, and housed at 23° C.±5° C. and 55%±5% relative humidity throughout the experiment.

Blood samples were obtained by puncture of the eye vein and white blood cells and platelets were counted automatically on a hematology analyzer (MEK6300, Japan). Peripheral blood counts are depicted as average values plus or minus SEM. To obtain bone marrow samples, mice were killed by cervical dislocation after isoflurane anesthesia. Bone marrow cells were harvested by flushing two femur and tibia bones with IMDM medium.

Peripheral blood samples were obtained by retro-orbital bleeding of 1 mL peripheral blood. Each blood sample was coagulated in the refrigerator at 4° C. and centrifuged at 1000×g for 15 min. The serum was collected and stored at −70° C. Aliquots were used once only and were not subjected to repeated freeze-thaw cycles. ELISAs were performed according to manufacturer's instructions (Quantikine Immunoassays, Cat. No. MRA00, by R&D System, USA).

Bone marrow mononuclear cells were isolated from mouse femurs by Ficoll gradient centrifugation. Briefly, the cells were fixed in 50% ethanol 1 h before FACS. The cells were centrifuged and resuspended in 0.4 ml of PBS, 5 mM EDTA containing 20 μg RNaseA and 20 μg propidium iodide (PI) (Sino-American Biotec, Beijing, China). G1, G2 and S phases of the cell cycle were analyzed using the FACS Calibur flow cytometer (Becton Dickinson, USA).

Results were statistically analyzed using a Student t test or one-way ANOVA analysis. The results are expressed as mean value plus or minus standard error of the mean (SEM). P less than 0.05 was considered significant.

2. Production of Recombinant Murine IL-1Ra

Recombinant murine IL-1Ra polypeptides were produced in *E. coli* according to the procedures described in this Example. Using the methods described below, it would also be possible for the skilled artisan to generate and/or compare additional IL-1Ra polypeptides, variants, or fragments to the ones described here.

rMuIL-1Ra was produced in *E. coli* using a plasmid-based expression vector. The sequence of rMuIL-1Ra lacing the signal peptide is shown in Table 3 (SEQ ID NO: 2) (GenBank Accession No. AAA39309). The protein was expressed in insoluble inclusion bodies within the *E. coli* cells. The expression vector pET28a (+) and its host strain *E. coli* BL21 (DE3) were purchased from Novagen. RT-PCR kits and DNA polymerase (KOD plus) were purchased from Toyoba Company (Japan). The IL-1Ra cDNA was reverse transcribed from total RNA isolated from C57BL/6b mouse bone marrow cells.

TABLE 3

Amino acid sequence of murine IL-1Ra (SEQ ID NO: 2)

MRPSGKRPCKMQAFRIWDTNQKTFYLRNNQLIAGYLQGPNIKLEEKIDMV

PIDLHSVFLGIHGGKLCLSCAKSGDDIKLQLEEVNITDLSKNKEEDKRFT

FIRSEKGPTTSFESAACPGWFLCTTLEADRPVSLTNTPEEPLIVTKFYFQ

EDQ

PCR primers were designed according to the murine IL-1Ra cDNA sequence and synthesized by Sangon (China). The forward primer contained an engineered NcoI site 5'-CATGCCATGGCACGCCCTTCTGGGAAAA-3 (SEQ ID NO:3), and the reverse primer incorporated an engineered BamHI site 5'-CGGGATCCCTATTGGTCTTCCTGGAAG-TAGAA-3' (SEQ ID NO:4). To avoid the His-tag and T7-tag of the vector, the NcoI site was chosen to contain ATG translation start codon. To construct the coding sequence of mature MuIL-1Ra in frame with ATG, and connect to the extra G in the NcoI site, an extra amino acid Ala (A) was created by addition of CG to the 5' IL-1Ra coding sequence.

These PCR primers were used to amplify the murine IL1-Ra as follows. After denaturation for 2 min at 94° C., amplification was performed for 35 cycles consisting of 20 s at 94° C., 30 s at 56° C., and 40 s at 68° C. The purified PCR product and pET28a vector were digested with NcoI and BamHI (Fermentas, U.S.), gel-purified, and ligated together. E. coli DH5α was chemically transformed with the recombinant vector and cultured at 37° C. in LB agar with kanamycin (100 µg/ml) for selection of recombinants. The recombinant plasmid containing the insert was named pET28a-IL-1Ra. Recombinants were verified by restriction enzyme digestion and DNA sequencing (Invitrogen, China).

E. coli BL21 (DE3) cells were transformed with the plasmid pET28a-IL-1Ra. A single transformed BL21 colony was inoculated into 3 mL LB medium supplemented with kanamycin (100 µg/ml) and grown with 250 rpm shaking overnight at 37° C. One hundred microliters (100 µl) of culture was transferred to 3 ml fresh LB medium in a 10 mL tube. The culture was grown with 250 rpm shaking at 37° C. until the $OD_{600}$ reached 1.0 and then 3 µl of 500 mM IPTG was added for induction.

The protein samples were analyzed by SDS-PAGE and protein staining SDS-PAGE was performed using a 12% resolution gel on the PowerPac Basic (Bio-Rad). Briefly, the protein samples were loaded on the gel, which was electrophoresed at 120 V for 1 h and then stained with Coomassie brilliant blue R-250. FIG. 1A shows the expression of rMuIL1-Ra in crude extract. Lane 1 is the uninduced E. coli cell lysate and Lane 2 is the lysate from cells induced with IPTG. The rMuIL-1Ra is indicated by the arrow in the figure.

Figure 1B:
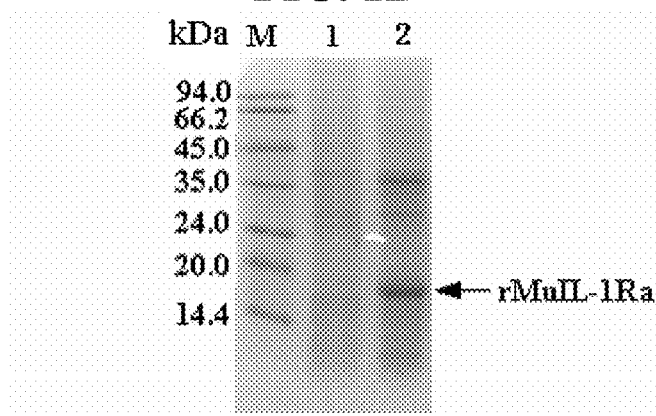

The inclusion bodies were found to contain most of the rMuIL1-Ra. FIG. 1B shows an SDS-PAGE of the supernatant and pellet following sonication (lanes 1 and 2, respectively). To prepare the inclusion bodies, the cell pellet was resuspended in the lysis buffer (1×PBS, 1 mM EDTA, 0.1 mM PMSF) at a final concentration of 50 mg/ml and sonicated (SANYO soniprep 150, 15 bar; 30 s working and 30 s resting on ice for a cycle, 18 cycles). After centrifugation at 12,000 g for 15 min at 4° C., the undissolved inclusion bodies were collected and washed with pellet wash buffer (0.5% Triton X-100, 10 mM EDTA, 50 mM NaCl) at 12,000 g for 5 min at 4° C., 5 times. The inclusion bodies were then solubilized in Buffer U (20 mM $Na_2HPO_4$, 1 mM EDTA, 50 mM NaCl, pH 9.0) containing 8 M urea at 9 mL urea/g pellet, shaking slightly at 37° C. for 1 h. The insoluble pellets were removed by centrifugation at 15,000 g for 20 min at 4° C., and the dissolved inclusion bodies were ready for further purification.

The refolding was carried out by drop-wise dilution into defined protein folding buffer. The protein solution was dropped by adding a 10-fold volume of refolding buffer (20 mM $NaPO_4$, 1 mM EDTA, pH 6.0), under vigorous (magnetic stirrer) agitation. pH of the solution was maintained at 6.0. An equal volume dilution buffer (20 mM $NaPO_4$, 1 mM EDTA, pH 8.5) was added into the folding buffer. The refolded protein solution was incubated at 4° C. for about 24 h.

Figure 1C:
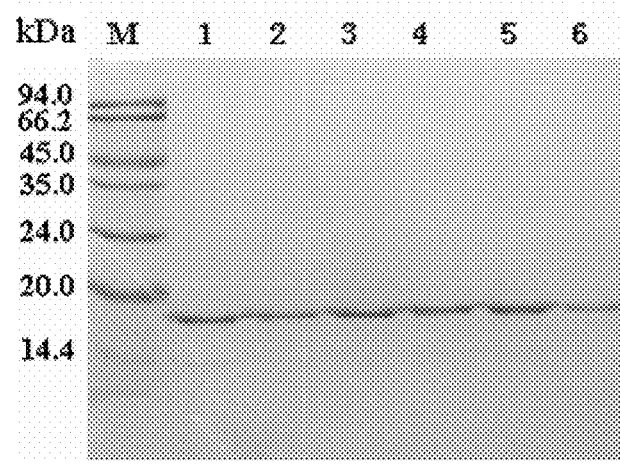

The refolded protein solution was centrifuged at 18,000 g for 30 min. The collected supernatant was loaded onto an S-Sepharose column with a volume of approximately 20 mL. The column was pre-equilibrated with Buffer A (20 mM $NaPO_4$, 1 mM EDTA, pH 7.2). The sample was loaded at speed of 0.5 ml/min and the column was then washed with 2 column volumes of Buffer A until the absorbance at 280 nm returned to baseline indicating removal of unbound protein. The column-bound proteins were eluted using a programmed gradient of Buffer B (20 mM $NaPO_4$, 1 mM EDTA, 1 M NaCl, pH 7.2) at a speed of 3 ml/min.

rMuIL-1Ra was further purified using anion exchange chromatography (Q Sepharose column). The recombinant protein was eluted by slowly increasing ionic strength of the buffer from 1M NaCl Buffer B. The flow speed was 1 ml/min. One peak of activity eluted from the anion-exchange column. The peak appeared when the conductivity reached 35 mS/cm. The results of the purification are shown in FIG. 1C. Protein samples from the fractions at the UV absorbance peak are shown in lanes 1-6. The final yield of rMuIL-1Ra was 13.4% compared to the starting protein. Endotoxin levels of purified IL-1Ra were undetectable. The purified protein was stored as a frozen solution, and prior to administration the IL-1Ra was diluted to the appropriate.

Example 2

Myelosuppressive Function of IL-1Ra in Hematopoeisis

In this Example, the myelosuppressive function of IL-1Ra in hematopoiesis was investigated in normal mice by administering to mice a recombinant form of murine IL-1Ra.

1. Dose Studies

Figure 2A:
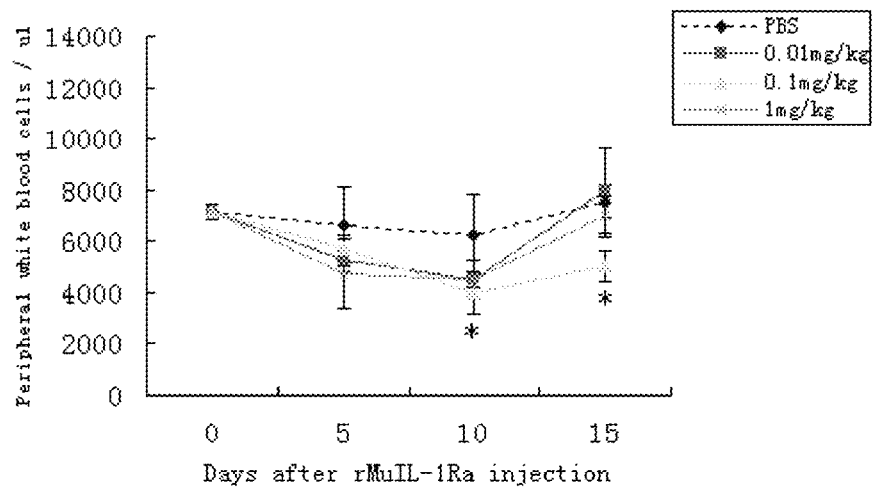
FIGS. 2A-C shows graphs of hematological blood cell indices—WBC (FIG. 2A), platelets (FIG. 2B) and bone marrow cells (FIG. 2C)—in normal mice administered varying dosages of recombinant IL-1Ra.
Figure 2B:
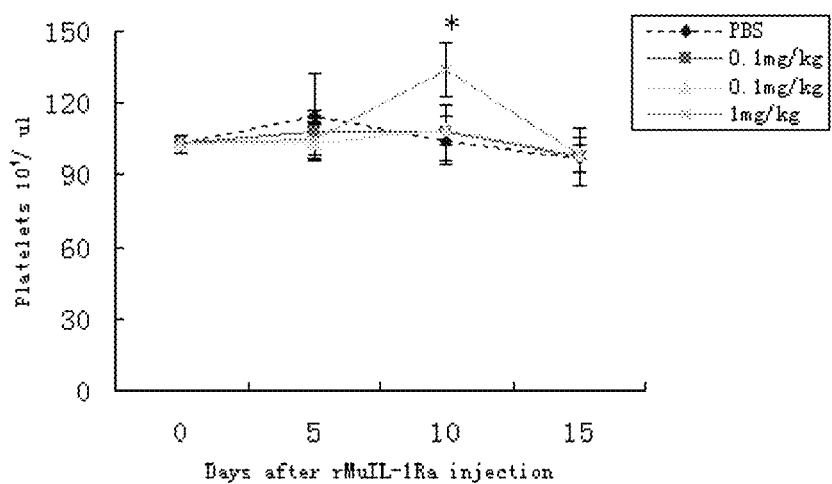
Figure 2C:
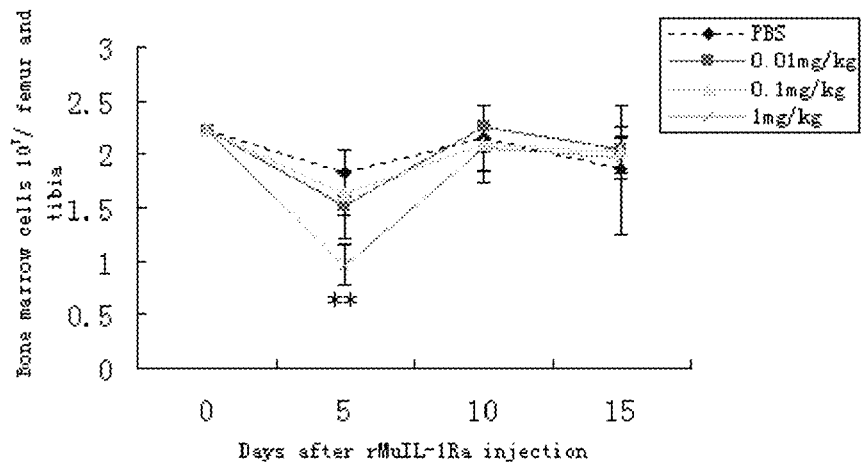

In order to determine the effect of rMuIL-1Ra on hematopoiesis, a dosage course for effects of rMuIL-1Ra in normal mice was determined. rMuIL-1Ra was diluted to the desired concentration in phosphate buffered saline (PBS), pH 7.4. Normal mice were treated with a daily subcutaneous injection of rMuIL-1Ra for 5 consecutive days at three different doses (0.01, 0.1, or 1 mg/kg of body weight) and were assayed at various times post-treatment. Control mice were given only PBS. On days 5, 10, and 15 following rMuIL-1Ra treatment, mice were sacrificed by cervical dislocation and their hematological blood cell indices (WBC, platelets and bone marrow cells) were evaluated. FIG. 2 shows the results of the experiments. FIG. 2A shows the number of white blood cells from 1 µl of peripheral blood. A significant difference appeared between the 0.1 mg/kg group and the control group as indicated by * at day 10 and day 15 ($p^* < 0.05$ by one-way ANOVA). FIG. 2B and Table 4 show the number of platelets in 1 µl of peripheral blood. A significant difference appeared between the 1 mg/kg group and the control group as indicated by * at day 10 ($p^* < 0.05$ by one-way ANOVA). FIG. 2C and Table 5 show the total bone marrow cells from one femur and one tibia of each mouse. At day 5, rMuIL-1Ra groups of the highest doses showed decreased cells counts compared to the control group, but that was recovered rapidly at day 10 ($p^{**} < 0.01$ by one-way ANOVA (n=4~6)). These results indicate that the administration of rMuIL-1Ra at various dosages results in decreased BM and peripheral WBC production in mice (FIGS. 2A, 2C), but surprisingly results in increased thrombopoiesis (FIG. 2B).

TABLE 4

Dose-dependent efficacy of IL-1Ra on platelets in normal mice

| Dose (mg/kg) | Day 0 | Day 5 | Day 10 | Day 15 |
|---|---|---|---|---|
| PBS | 102.83 ± 3.68 | 114.57 ± 17.66 | 104.4 ± 9.82 | 96.63 ± 5.77 |
| 0.01 | 102.83 ± 3.68 | 107.93 ± 9.31 | 107.7 ± 11.66 | 97.47 ± 12.34 |
| 0.1 | 102.83 ± 3.68 | 103.5 ± 7.88 | 108.8 ± 6.0 | 98.13 ± 2.04 |
| 1 | 102.83 ± 3.68 | 104.6 ± 7.71 | 133.9 ± 11.59* | 98.37 ± 7.31 |

TABLE 5

Dose-dependent efficacy of IL-1Ra on bone marrow cells in normal mice ($\times 10^6$)

| Dose (mg/kg) | Day 0 | Day 5 | Day 10 | Day 15 |
|---|---|---|---|---|
| PBS | 22.27 ± 0.46 | 18.27 ± 2.21 | 21.5 ± 1.32 | 18.57 ± 6.06 |
| 0.01 | 22.27 ± 0.46 | 15.17 ± 3.02 | 22.53 ± 2.07 | 20.37 ± 2.2 |
| 0.1 | 22.27 ± 0.46 | 16.3 ± 1.99 | 21 ± 3.6 | 20.2 ± 1.59 |
| 1 | 22.27 ± 0.46 | 9.67 ± 1.98** | 20.63 ± 2.2 | 19.63 ± 1.89 |

2. Time Course Study

The time course for effects of rMuIL-1Ra on hematopoiesis in normal mice was determined. Mice were administered rMuIL-1Ra (1 mg/kg) subcutaneously daily and were sacrificed at four time points (days 1, 2, 4, and 6). Femoral bone marrow was harvested and assayed for their bone marrow cells counts. The bone marrow mononuclear cells were separated and collected for cell-cycle analysis by FACS at every time point.

Figure 3:
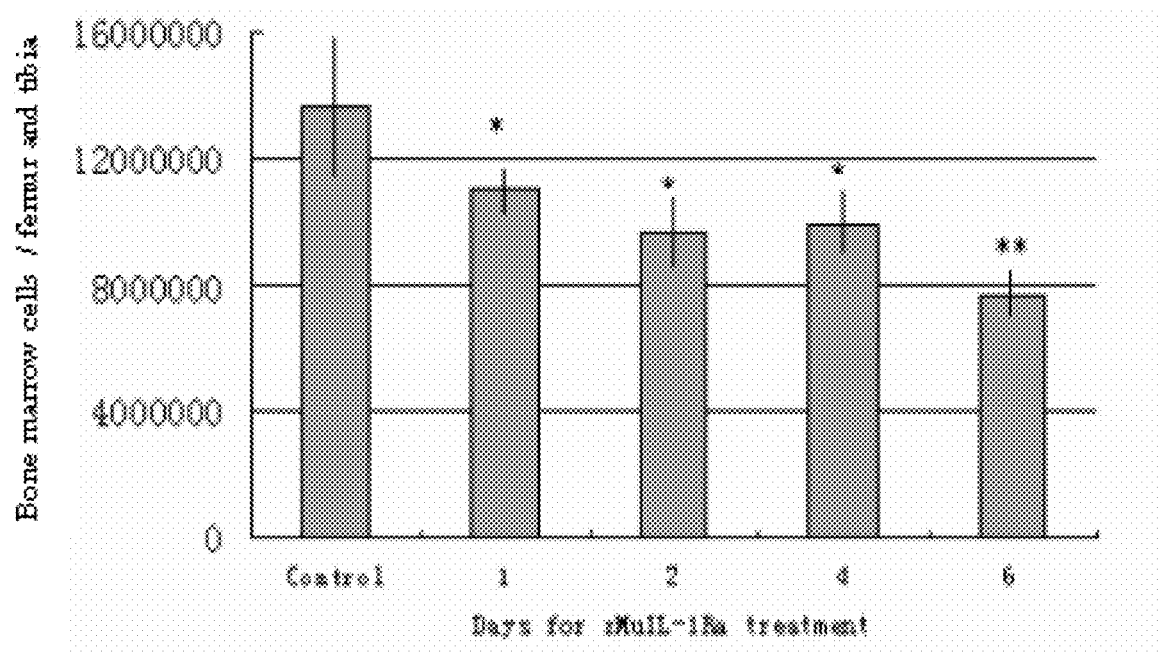
FIG. 3 shows a graph of bone marrow density in mice administered a time-course of recombinant IL-1Ra.

FIG. 3 shows the effects of rMuIL-1Ra on the number of bone marrow cells in response to the injection of rMuIL-1Ra for different time periods. Mean bone marrow cells counts show a steady decrease over the treated time period, compared with the control group. These differences achieved statistical significance at day 6.

Figure 4A:
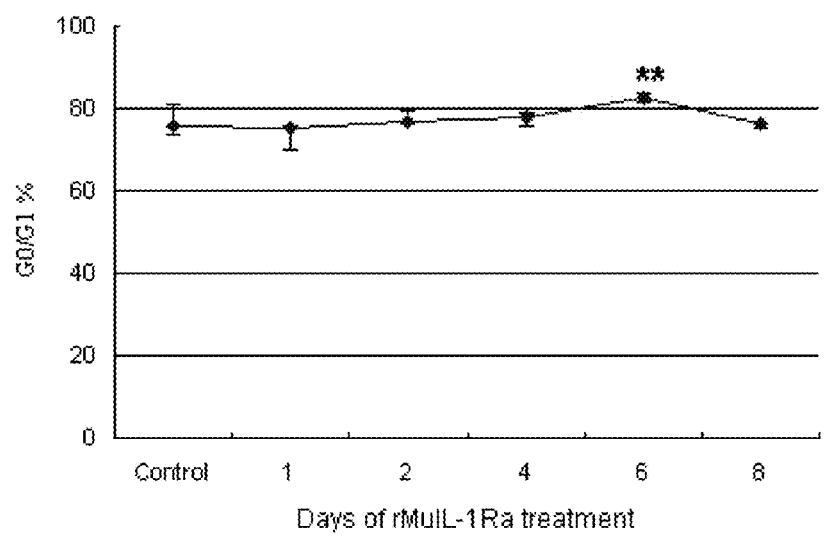
FIGS. 4A-C shows graphs of FACS results indicating the percentage of cells at each stage of the cell cycle following administration of rMuIL-1Ra to mice.
Figure 4B:
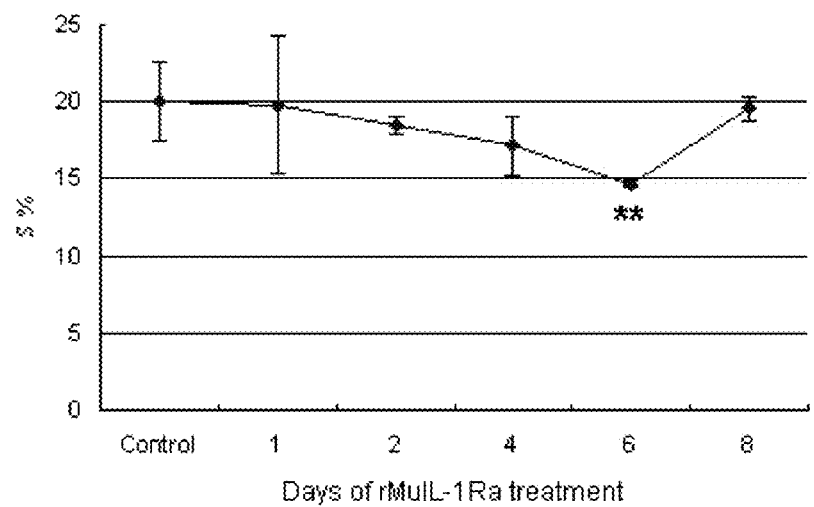
Figure 4C:
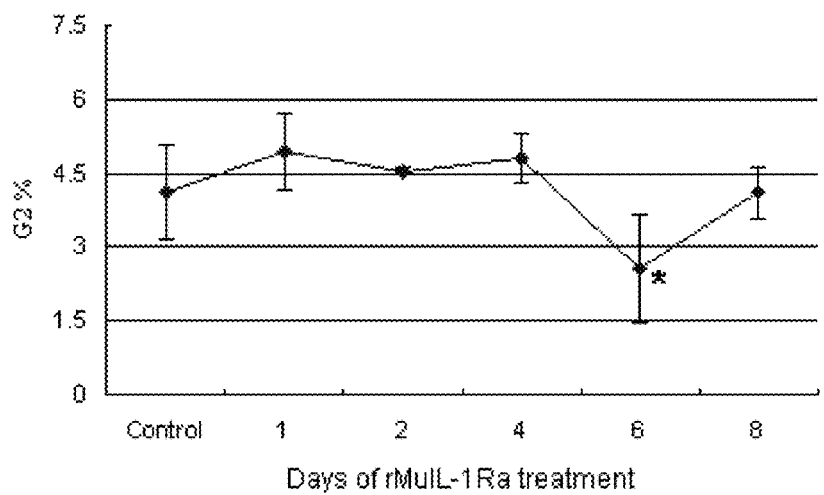
Figures 5A, 5B:
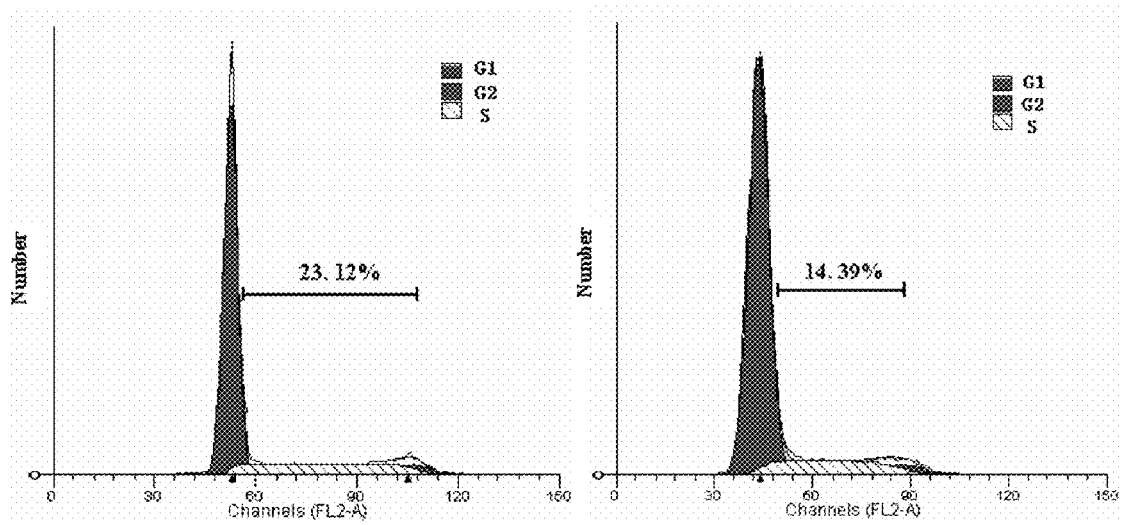
FIGS. 5A-B shows FACS results indicating the percentage of cells in the S phase of the cell cycle after 6 days of rMuIL-1Ra administration.

FACS analysis was used to determine the effect of rMuIL-1Ra treatment on cell cycle progression of hematopoietic cells. The FACS results show that the administration of rMuIL-1Ra prevents entrance of bone marrow monocytes into cell cycle (FIG. 4, Table 6). According to FIG. 5B, after 6 days of rMuIL-1Ra treatment, significantly fewer cells entered S phase compared to the control group. Likewise, a significantly increased number of cells were in the G0/G1 phase after 6 days of treatment (FIG. 4A, Table 6).

TABLE 6

FACS Analysis of Bone Marrow Monocytes after 5 Days of rMuIL-1Ra

| Different phase | Control | rMuIL-1Ra |
|---|---|---|
| G0/G1 (%) | 75.83 ± 2.03 | 80.79 ± 0.00, ** |
| S (%) | 20.06 ± 2.58 | 14.67 ± 0.00, ** |
| G2 (%) | 4.11 ± 0.97 | 2.54 ± 0.04, * |

The results indicate that IL-1Ra directs hematopoietic cells to enter the quiescent phase of the cell cycle. Cells in the $G_0/G_1$ phase of the cell cycle would be resistant to the toxic effects associated with cell cycle-specific chemotherapeutic agents, e.g. 5-FU. Accordingly, IL-1Ra may be used in the methods of the present invention to protect cells from the toxic effects of chemotherapeutic agents—in particular, chemotherapeutic agents that are cell cycle-specific.

Example 3

Expression of IL-1Ra and IL-1β Following Chemotherapy

To investigate the biological function of IL-1Ra in hematopoiesis, plasma samples from mice at several time points following 5-FU administration were assayed for IL-1Ra and IL-1β expression. Specifically, mice of 7-8 weeks of age were injected with 5-FU at a dose of 250 mg/kg via the tail vein. The sera of mice were analyzed at 3, 7, 11, and 14 days post injection using Affymetrix gene expression profiling and ELISA analysis of IL-1Ra and IL-1β protein expression.

For Affymetrix Gene Chip analysis, five total RNA samples were extracted from bone marrow cells collected at days 0, 3, 7, 11, and 14 days post-5-FU treatment. Bone marrow cells from 5-20 mice were used for each time point to collect enough cells for RNA extraction. Equal amounts of poly(A) RNA from each sample were used to synthesize double-stranded cDNA. Five cRNA probes were prepared by in vitro transcription using an equal amount of cDNA from the five samples. Equal amounts of probes were used for hybridization to mouse genome expression oligonucleotide arrays (GeneChip mouse expression set 430, Affymetrix, Santa Clara, Calif.) containing 34,323 well-substantiated mouse genes. The hybridization intensity information was gathered using a GeneChip Scanner 3000 and analyzed with Affymetrix Microarray Suite Version 5.1 (Affymetrix, Santa Clara, Calif.). A global scaling strategy was used for all arrays that set the average signal intensity of the array to a target signal of 5000. Comparison analyses for expression data at each time point were calculated by using a day 0-array as a baseline.

Protein expression was evaluated using an ELISA kit for IL-1Ra and IL-1β, according to the manufacturer's instructions (Quantikine Immunoassays, Cat. Nos. MRA00/MLB00B, by R&D Systems, USA).

Figure 6A:
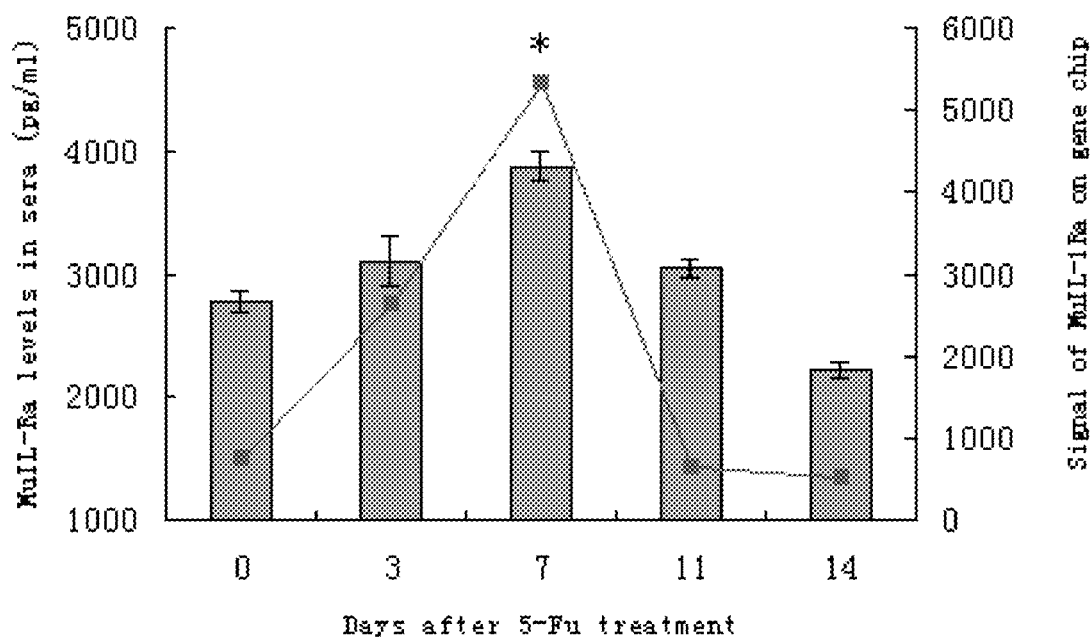
FIGS. 6A-B shows RNA and protein expression data, as measured by Affymetrix Gene Chip and ELISA, respectively, of IL-1Ra (FIG. 6A) and IL-1β (FIG. 6B) following treatment with 5-FU.
Figure 6B:
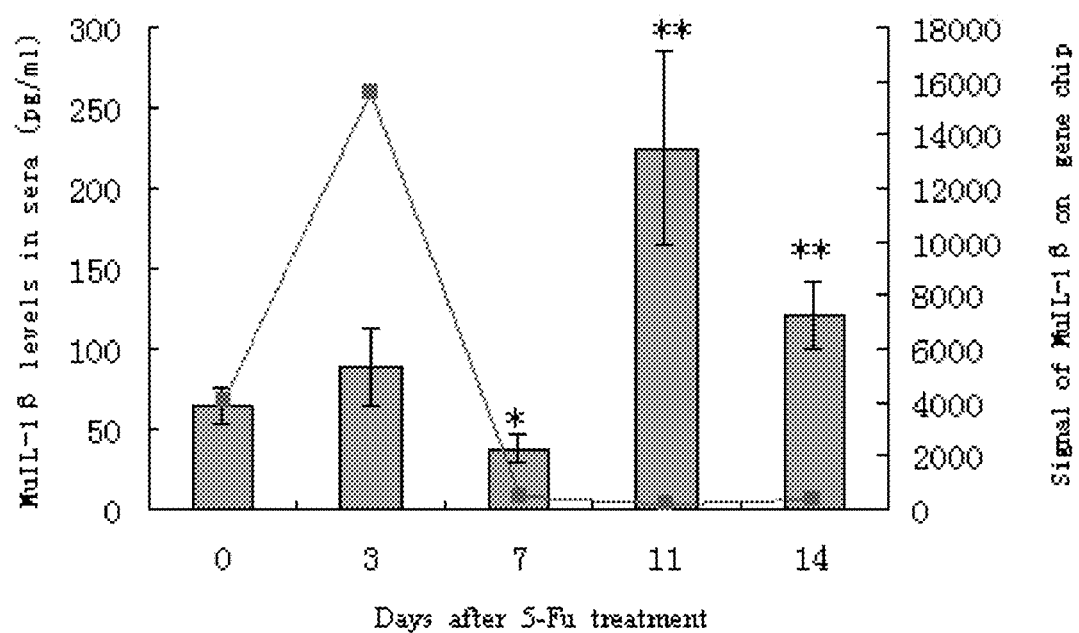

As shown in FIG. 6A, the level of IL-1Ra expression increased after chemotherapy, until a peak at day 7. Both ELISA and microarray data indicate that at day 7 the concentration of IL-1Ra was significantly higher than at day 0. The level of IL-1Ra protein expression began to decrease after day 7, and reached the baseline at day 14. As shown in FIG. 6B, the level of IL-1β expression was steady until day 7, after which IL-1β expression increased—reaching a peak at day 11.

IL-1Ra was shown to be a hematopoietic inhibitor (see Example 2) and the data in this example show that IL-1Ra is upregulated after 5-FU treatment. Thus, the overexpression of endogenous IL-1Ra is likely responsible for the observed suppression of hematopoiesis after chemotherapy, indicating that IL-1Ra upregulation is part of the subject's natural response to bone marrow insults. By directing the bone marrow to enter a quiescent stage following one insult, the subject is thereby resistant to further insults. Therefore, these results suggest that the use of IL-1Ra before chemotherapy, to prepare the bone marrow to tolerate the toxic effects of chemotherapy, would allow for greater doses of chemotherapeutic agents to be administered.

Example 4

Myeloprotective Effects of IL-1Ra in a Murine Model of Chemotherapy

The ability of the IL-1Ra compositions of the invention to provide a therapeutic benefit to mice receiving chemotherapy was investigated. In this Example, rMuIL-1Ra was administered to mice on various schedules. The number of bone marrow cells, peripheral white blood cells, and platelets was counted at several time points following administration of 5-FU (See Table 7).

TABLE 7

Experimental Treatment Groups

| Treatment | Group/Treatment Schedule | | | | |
|---|---|---|---|---|---|
| | A | B | C | D | E |
| rMuIL-1Ra (1 mg/kg) | | | | | |
| Days | −5~−1 | 1~5 | −2~2 | −2~−1 | 7~11 |

1. Effects of IL-1Ra Administration for Five Days Prior to Chemotherapy rMuIL-1Ra was prepared as described in Example 1 and diluted in PBS, pH 7.4. Mice were administered the rMuIL-1Ra (1 mg/kg) subcutaneously for five consecutive days. Twenty-four hours after the last injection of rMuIL-1Ra, the mice were administered 5-FU (250 mg/kg). Control mice were given only PBS prior to 5-FU injection. Animals were then serially sacrificed (on days 0, 3, 7, 11 and 14 following chemotherapy) and their peripheral blood and bone marrow were analyzed.

Figure 7A:
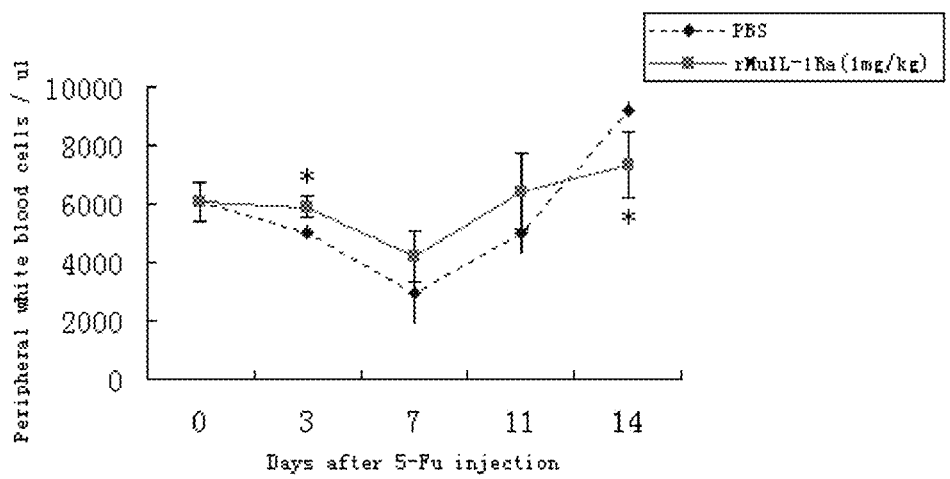
FIGS. 7A-C shows graphs of hematological blood cell indices—WBC (FIG. 7A), platelets (FIG. 7B) and bone marrow cells (FIG. 7C)—in mice which were administered rMuIL-1Ra for 5 days prior to receiving chemotherapy. Samples were taken at various time points up to 14 days after chemotherapy.
Figure 7B:
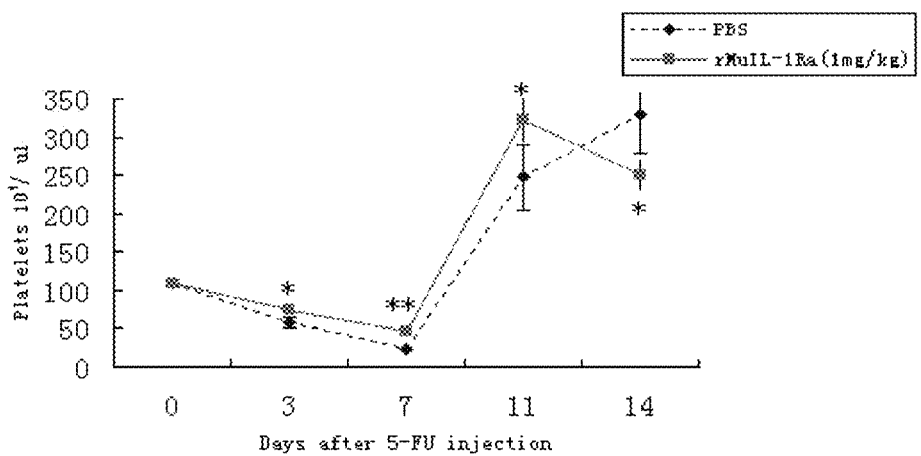
Figure 7C:
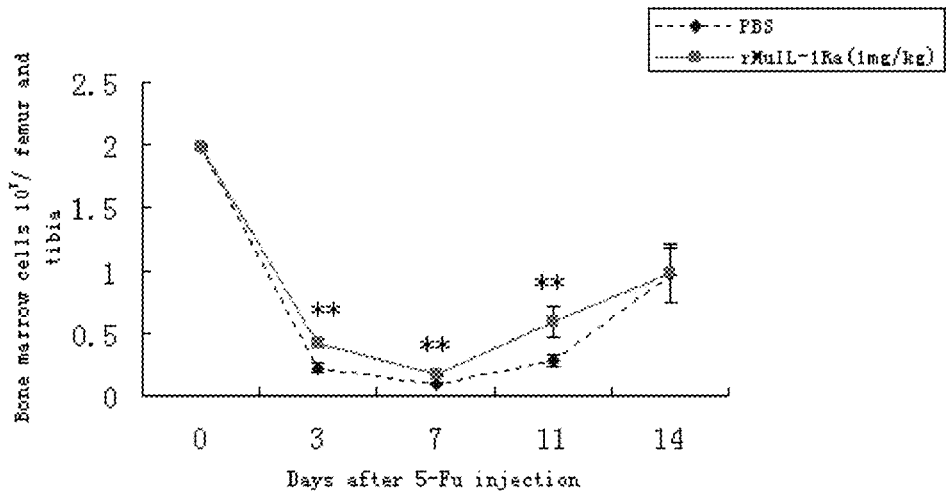

The results are shown in FIG. 7. In FIG. 7A, white blood cells from 1 μl of peripheral blood were quantified. A significant difference appeared between the rMuIL-1Ra group and the control group as indicated by * at day 3 and day 14 (p*<0.05 by one-way ANOVA). In FIG. 7B, platelets from 1 μl of peripheral blood were quantified. The figure shows that at day 3, 7, and 11, rMuIL-1Ra groups recovered better than the control PBS group (p*<0.05 by one-way ANOVA). In FIG. 7C, bone marrow cells from one femur and one tibia were quantified. The control PBS group had lower cells counts than rMuIL-1Ra group at days 3, 7 and 11 (p**<0.01, n=4~6), also indicating a more rapid hematopoietic recovery following chemotherapy.

Thus, the data demonstrate the ability the IL-1Ra polypeptides used in the methods of the invention to influence the recovery of various blood indices following 5-FU. There were dramatic changes observed in the recovery for both the platelets and bone marrow cells counts when compared to the control group. rMuIL-1Ra was able to prevent the development of thrombocytopenia and to a lesser extent neutropenia. As such, the IL-1Ra protein is useful in the methods of the invention as a myeloprotectant against chemotherapy.

2. Effects of IL-1Ra Administration for Five Days after Chemotherapy rMuIL-1Ra was prepared as described in Example 1 and diluted in PBS, pH 7.4. Mice received a single i.v. injection of 5-FU (250 mg/kg of body weight). Twenty-four hours after the 5-FU injection, mice were administered the rMuIL-1Ra (1 mg/kg) subcutaneously for five consecutive days. Control mice were given only PBS prior to 5-FU injection. Animals were then serially sacrificed (on days 0, 3, 7, 11 and 14 following chemotherapy) and their peripheral blood and bone marrow were analyzed.

Figure 8A:
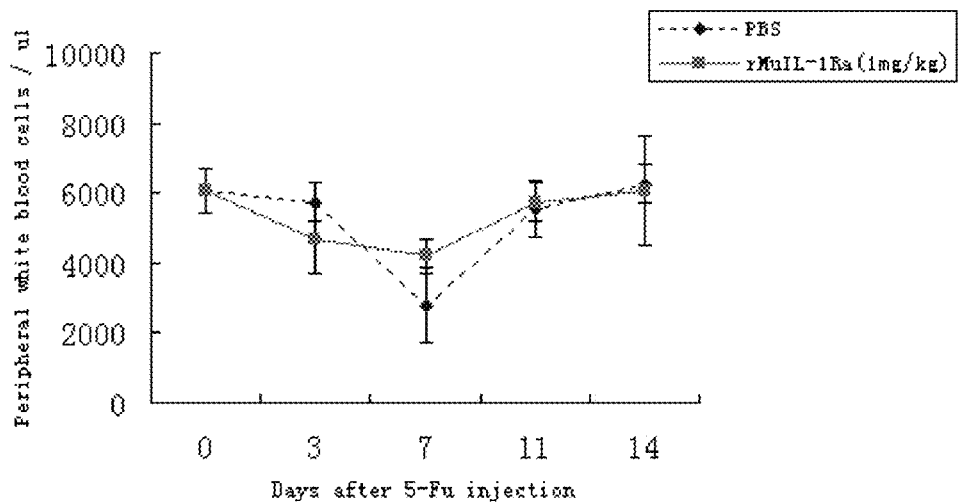
FIGS. 8A-C shows graphs of hematological blood cell indices—WBC (FIG. 8A), platelets (FIG. 8B) and bone marrow cells (FIG. 8C)—in mice which were administered rMuIL-1Ra for 5 days after receiving chemotherapy. Samples were taken at various time points up to 14 days after chemotherapy.
Figure 8B:
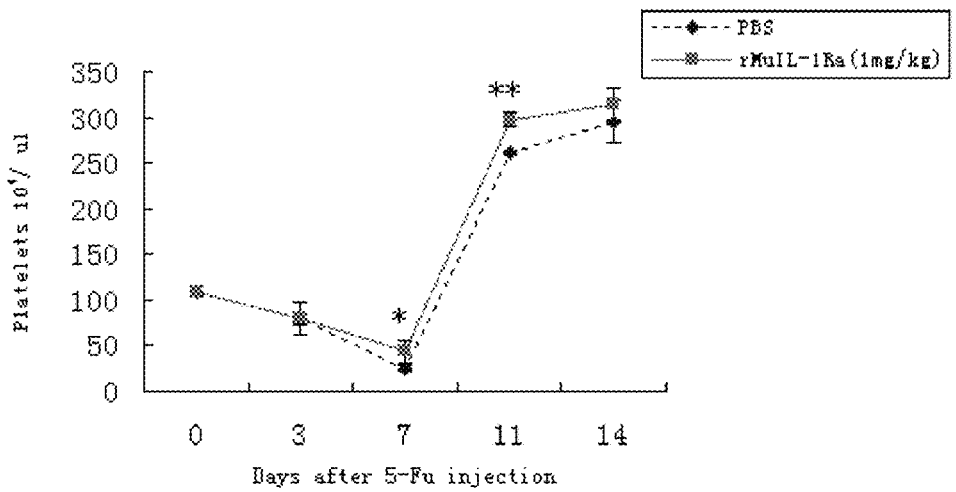
Figure 8C:
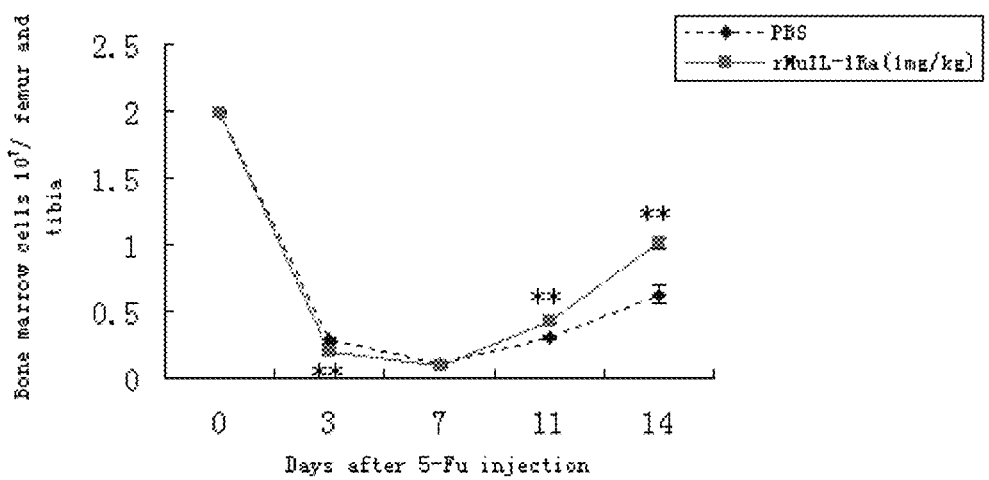

The results are shown in FIG. 8. In FIG. 8A, white blood cells from 1 μl of peripheral blood were quantified. A non-significant difference appeared between the rMuIL-1Ra group and the control group. In FIG. 8B, platelets from 1 μl of peripheral blood were quantified. The results show that at days 7 and 11, the rMuIL-1Ra groups recovered better than the control PBS group (p*<0.05 by one-way ANOVA). In FIG. 7C, bone marrow cells from one femur and one tibia were quantified. A significant difference appeared between the rMuIL-1Ra group and the control group as indicated by * at day 3, 11, and 14 (p**<0.01 by one-way ANOVA, n=4~6). A reduction at day 3, and increments at day 11 and 14 in bone marrow cells were observed in the rMuIL-1Ra group over the control.

Thus, the data demonstrate the ability the IL-1Ra polypeptides used in the methods of the invention to influence hematopoietic recovery after 5-FU administration. The number of bone marrow cells at day 3 after 5-Fu treatment is significantly lower in the rMuIL1-Ra group than the control group, which demonstrates that the use of rMuIL-1Ra after chemotherapy has a negative effect on bone marrow hematopoiesis. As such, these results support the use of IL-1Ra before chemotherapy.

3. Effects of IL-1Ra Administration for Two Days Before and Two Days after Chemotherapy rMuIL-1Ra was prepared as described in Example 1 and diluted in PBS, pH 7.4. Mice were administered the rMuIL-1Ra (1 mg/kg) subcutaneously for two consecutive days. Twenty-four hours after the second injection of rMuIL-1Ra, the mice were administered 5-FU (250 mg/kg). Control mice were given only PBS prior to 5-FU injection. Animals were then administered rMuIL-1Ra (1 mg/kg) subcutaneously for 2 consecutive days following 5-FU treatment. Animals were serially sacrificed (on days 0, 3, 7, 11, 14, 21, and 28 following chemotherapy) and their peripheral blood and bone marrow were analyzed. Control mice were given only PBS.

Figure 9A:
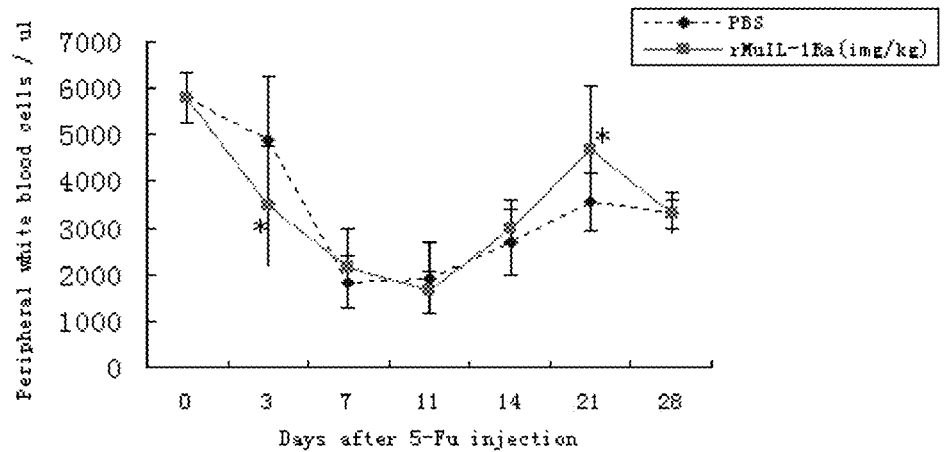
FIGS. 9A-C shows graphs of hematological blood cell indices—WBC (FIG. 9A), platelets (FIG. 9B) and bone marrow cells (FIG. 9C)—in mice which were administered rMuIL-1Ra for 2 days prior to and 2 days after receiving chemotherapy. Samples were taken at various time points up to 28 days after chemotherapy.
Figure 9B:
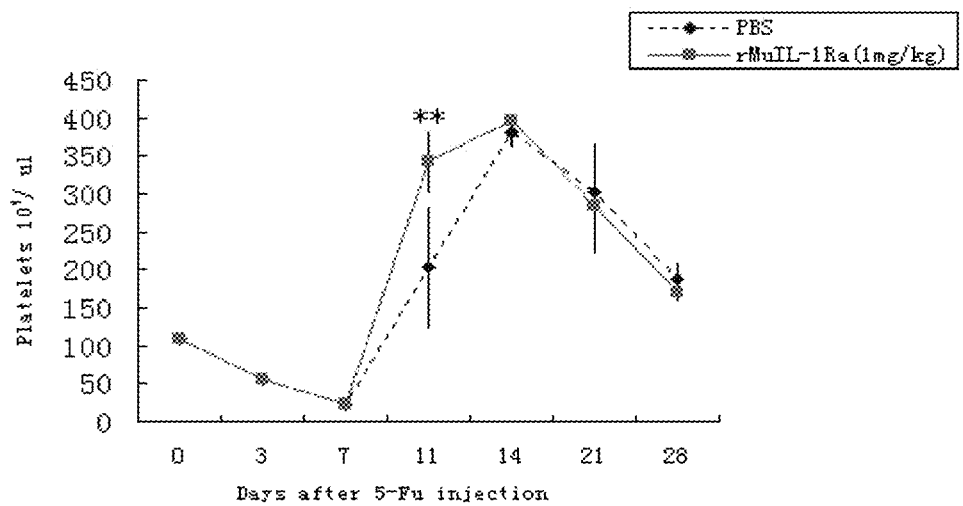
Figure 9C:
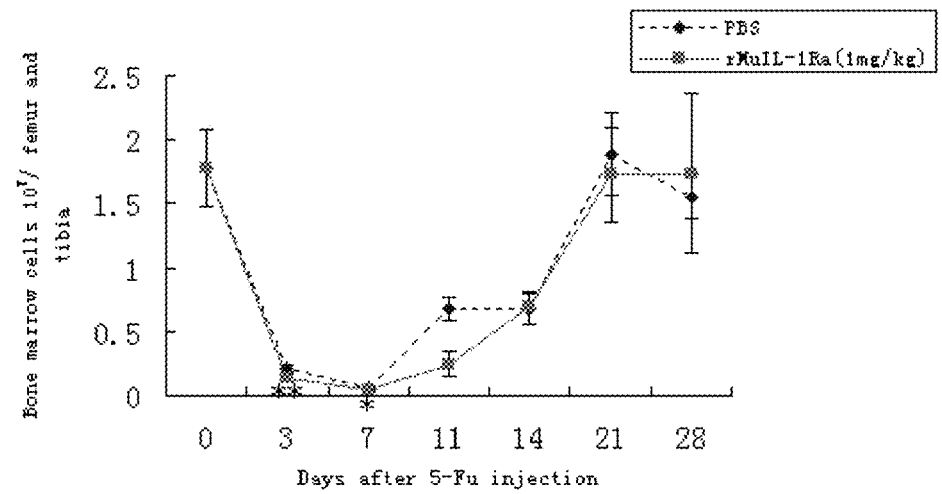

The results are shown in FIG. 9. In FIG. 9A, white blood cells from 1 μl of peripheral blood were quantified. At day 3, the rMuIL-1Ra group had lower cells counts than the control PBS group. At day 21, the rMuIL-1Ra group recovered better than the PBS control group (p*<0.05 by one-way ANOVA). In FIG. 9B, platelets from 1 μl of peripheral blood were quantified. The data show that at day 11 rMuIL-1Ra groups recovered better than the control PBS group (p**<0.01 by one-way ANOVA). In FIG. 9C, bone marrow cells from one femur and one tibia were quantified. The rMuIL-1Ra group had lower cells counts than control PBS group at day 3 and 7 (p*<0.05 by one-way ANOVA, n=4~6).

Thus, the data demonstrate the ability the IL-1Ra polypeptides used in the methods of the invention to influence hematopoietic recovery before and after 5-FU administration. The number of bone marrow cells at day 3 and 7 after chemotherapy were significantly lower in the rMuIL-1Ra group than the control group, which demonstrates that the use of rMuIL1Ra before and after chemotherapy has negative effect on bone marrow hematopoiesis. As such, these results support the use of IL-1Ra before chemotherapy.

4. Effects of IL-1Ra Administration for Two Days Before Chemotherapy rMuIL-1Ra was prepared as described in Example 1 and diluted in PBS, pH 7.4. Mice were administered the rMuIL-1Ra (1 mg/kg) subcutaneously for two consecutive days. Twenty-four hours after the last injection of rMuIL-1Ra, these mice were administered 5-FU (250 mg/kg). Control mice were given only PBS prior to 5-FU injection. Animals were then serially sacrificed (on days 0, 3, 7, 11 and 14 following chemotherapy) and their peripheral blood and bone marrow were analyzed.

Figure 10A:
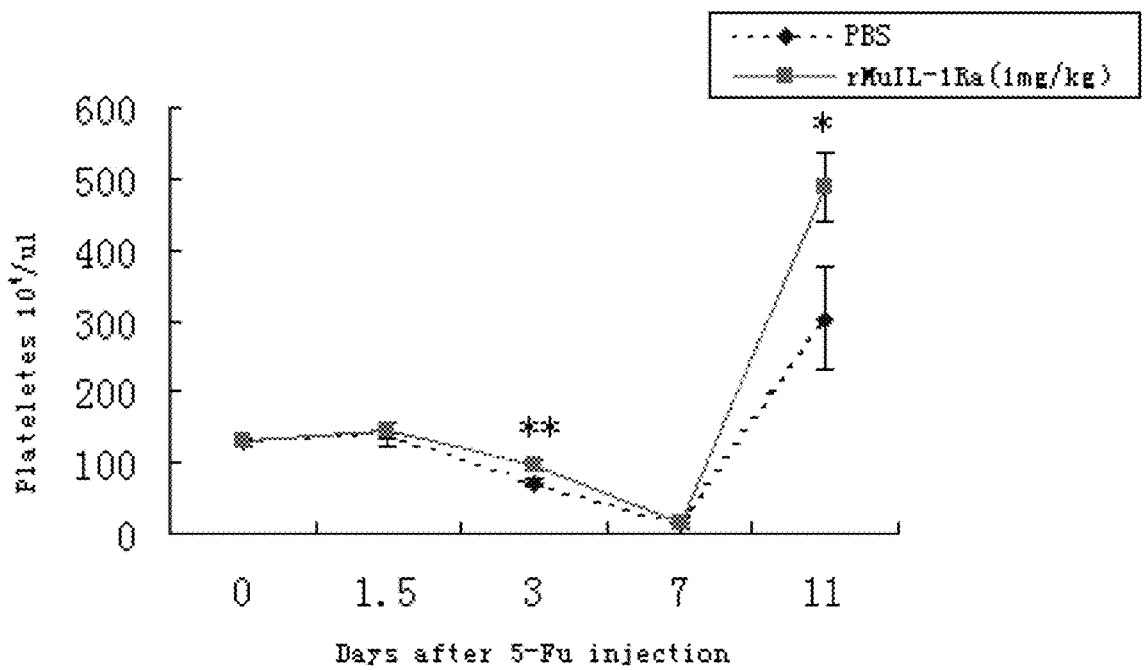
FIGS. 10A-B shows graphs of hematological blood cell indices—platelets (FIG. 10A) and bone marrow cells (FIG. 10B)—in mice which were administered rMuIL-1Ra for 2 days prior to receiving chemotherapy. Samples were taken at various time points up to 11 days after chemotherapy.
Figure 10B:
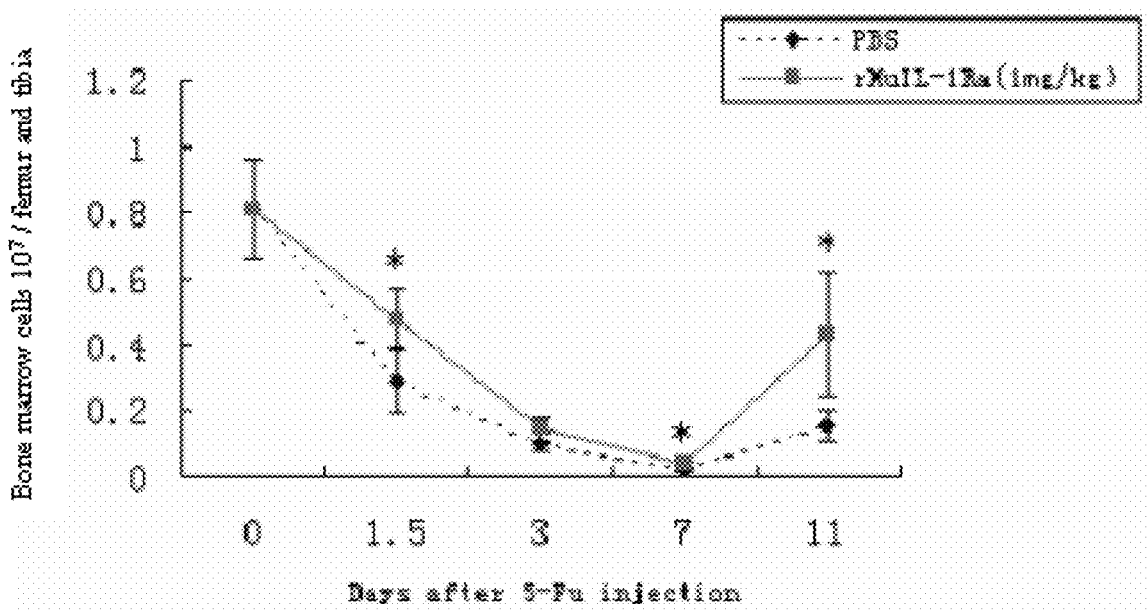

The results are shown in FIG. 10. In FIG. 10A, platelets from 1 μl of peripheral blood were quantified. The data show that at day 3 rMuIL-1Ra groups had higher cell counts than the control PBS group (p**<0.01 by one-way ANOVA). In FIG. 10B, bone marrow cells from one femur and one tibia were quantified. The rMuIL-1Ra group had higher cell counts than the control PBS group at day 1.5 and 7 (p*<0.05 by one-way ANOVA, n=4~6).

In all of these studies, the results show that rMuIL-1Ra was capable of significantly increasing the number of both bone marrow cells and platelets in chemotherapy subjects. However, administration of rMuIL-1Ra to mice before 5-FU is more myelostimulating, compared to rMuIL-1Ra administration after chemotherapy. Administration schedule studies also showed that the importance of the timing of rMuIL-1Ra administration for it to have an impact on platelet and bone marrow recovery after intensive chemotherapy. This schedule-dependent bone marrow recovery effect can be explained that use of rMuIL-1Ra before chemotherapy rendered the bone marrow cells arrests in $G_0/G_1$ phase, which are more resistant to 5-FU damage, as 5-FU targets cycling cells.

The results demonstrate that pretreatment with rMuIL-1Ra improved thrombocytopenia and myelosuppression induced by 5-FU, but post-treatment was less effective. In addition, a more pronounced effect was observed when rMuIL-1Ra was administered 5 days before 5-FU treatment rather than 2 days before 5-FU treatment (compare FIG. 7 and FIG. 10). Thus, these findings demonstrate the importance of the timing of pre-dosing to have maximal impact on the platelet and bone marrow nadir.

5. Enhanced Survival of Mice Administered IL-1Ra Prior to Chemotherapy

Figure 11:
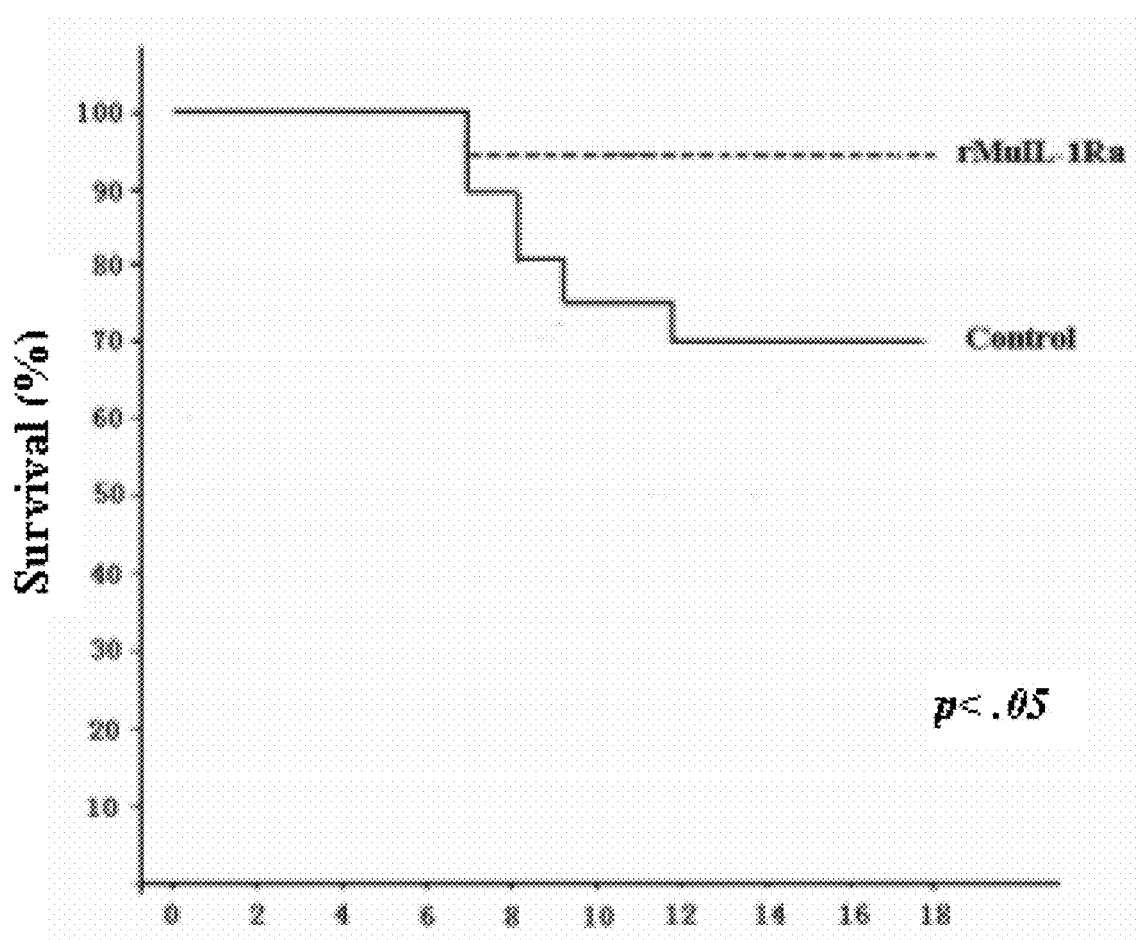
FIG. 11 shows a graph the survival of mice administered IL-1Ra (1 mg/kg) for two days prior to administration of a sub-lethal dose of 5-FU compared to control mice not administered IL-1Ra.

The protective effects of rMuIL-1Ra pretreatment against high doses of 5-FU was investigated. Improvement of survival following treatment of chemotherapeutic mice with rMuIL-1Ra for 2 days was investigated. Balb/c mice (30 per group) received a single dose of 5-FU (250 mg/kg) after 2 days rMuIL-1Ra (1 mg/kg). Survival was scored daily for 18 days. Log rank test and survival curves shows that chemotherapeutic mice given rMuIL-1Ra survived significantly (p<0.05) longer than chemotherapeutic mice that received PBS. Thus, the data demonstrate that pretreatment of mice for 2 days with rMuIL-1Ra (1 mg/kg) could protect 95% of the mice from the subsequent administration of a sub-lethal dose of 5-FU (FIG. 11). This chemoprotection by rMuIL-1Ra may allow an increased doses of 5-FU without adverse effects on survival.

6. Mechanism Study of IL-1Ra in Relating to its Effects of Platelets

Figure 12A:
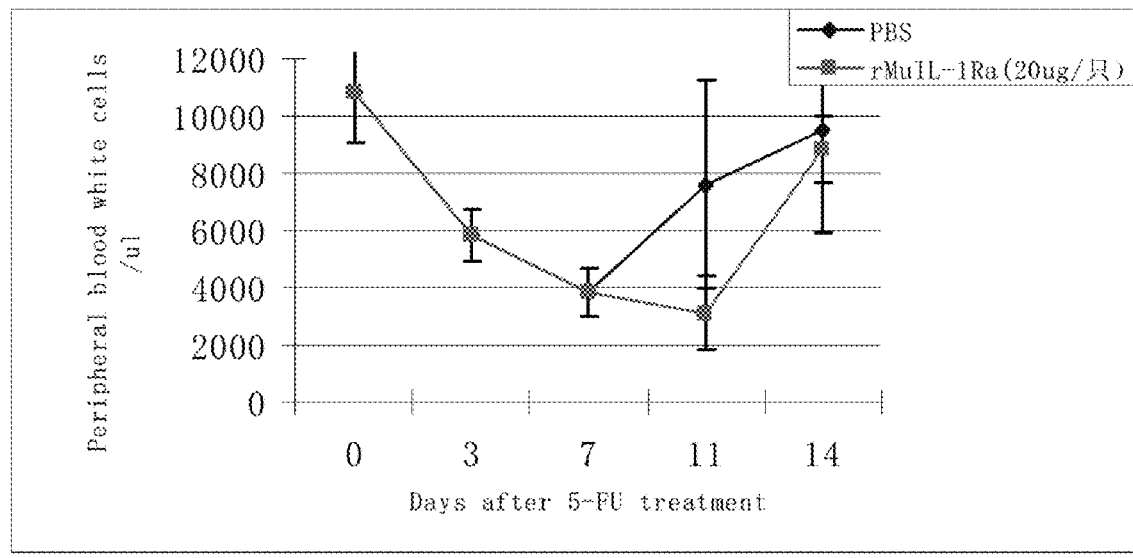
FIGS. 12A-B shows graphs of hematological blood cell indices—peripheral white blood cells (FIG. 12A) and platelets (FIG. 12B)—in mice which were administered rMuIL-1Ra for 7-14 days after receiving chemotherapy. Samples were taken at various time points throughout the 14 day period.
Figure 12B:
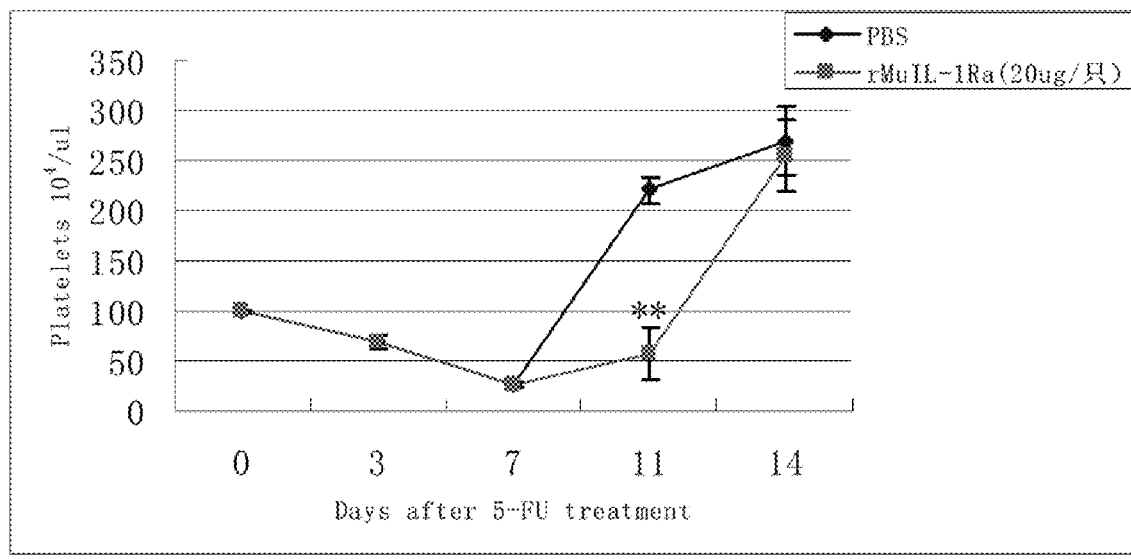
Figure 13:
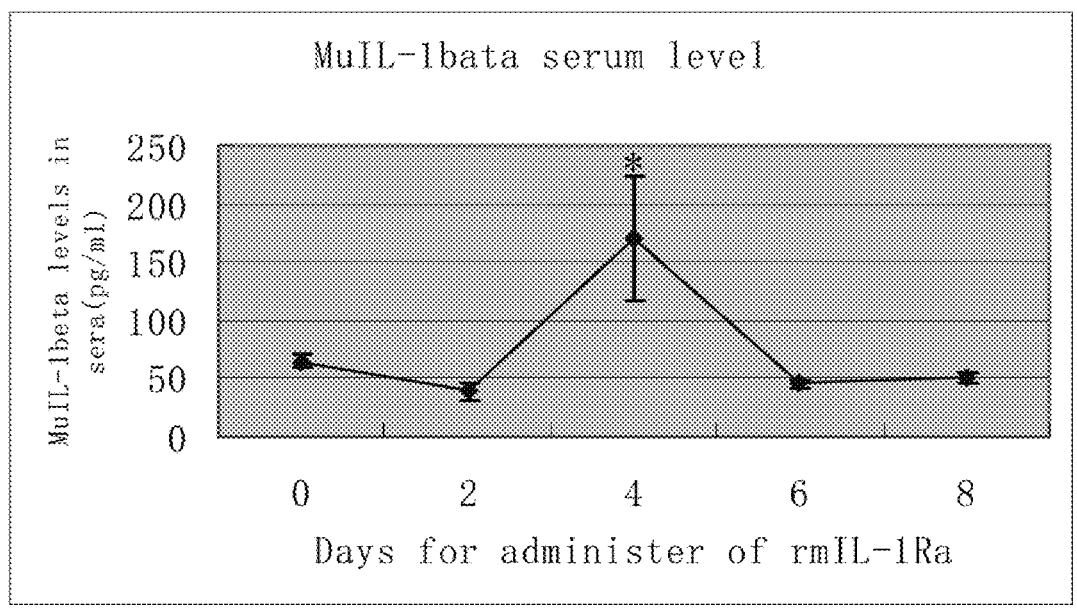
FIG. 13 shows a graph of the expression of IL-1β protein in mice receiving IL-1Ra for 0-8 days. The protein expression was measured using an ELISA assay.

In Example 2, it was observed that injection of IL-1Ra led to delayed increase in platelet counts. It was also shown that IL-1β expression is upregulated at the serum level during the recovery phase of hematopoiesis after chemotherapy (FIG. 6B). To investigate the interaction between IL-1Ra and IL-1β, recombinant IL-1Ra was administered at 7-14 days after 5-FU treatment to block the IL-1β action. The increase of platelet was completely suppressed (FIG. 12B). The increase in WBC was also suppressed, but to a lesser extent (FIG. 12A, trend only). During IL-1Ra administration, IL-1Rβ expression reaches a peak at day 4 (FIG. 13).

The data demonstrate that endogenous upregulation of IL-1β is responsible for the recovery (rebound) of platelet counts after 5-FU treatment. Taken together, the above examples indicate that the efficacy of IL-1Ra used to increase platelets before 5-FU is due to: (1) transient blocking existing IL-1β rendering the platelet-making cells resistant to 5-Fu damage; and (2) delayed upregulation of endogenous IL-1β accelerates the recovery of platelet indirectly. The activity of IL-1Ra can block the activity of IL-1β. Therefore, use of IL-1Ra before 5-FU, should suppress thrombopoiesis (the making of platelets) through antagonizing the endogenous IL-1β effects, rendering the megakaryocyte progenitors resistant to 5-FU. Consequently, after chemotherapy the megakaryocyte progenitors can quickly recover, leading to enhanced platelet production.

Example 6

Expression of Recombinant Human IL-1Ra

Recombinant human IL-1Ra polypeptides were produced in *E. coli* according to the procedures described in this Example. Using the methods described below, it would also be possible for the skilled artisan to generate and/or compare additional IL-1Ra polypeptides, or fragments or variants thereof to the ones shown in these examples.

1. Cloning of rhIL-1Ra Gene

The full length of secreted rhIL-1Ra gene (named as IL1RN, GenBank Accession No. M63099) is 534 by in length. The first 75 by encode a 25-amino acid signal peptide. A DNA fragment corresponding to by 75 to 534 in the gene IL1RN, which encodes 152 amino acid residues in the mature hIL-1Ra (Table 1, SEQ ID NO: 2), was cloned for protein expression in a prokaryotic system. The desired fragment was amplified by PCR from human liver cDNA using forward primer 5'-GGAATTCCATATGCGACCCTCTGG-GAGAAAATCC-3" (SEQ ID NO: 5) and reverse primer 5'-CGCGGATCCTTACTCGTCCTCCTGGAAGTAGA-3' (SEQ ID NO: 6) (synthesized by Sangon), which include sites for restriction enzymes NdeI and BamHI, respectively. PCR was performed in optimized conditions (95° C. for 5 minutes; 94° C. for 30 seconds, 55° C. for 30 seconds, 72° C. for 30 seconds, 32 cycles; 72° C. for 10 minutes). The resulting 500-bp fragment was cloned into pTA2 (Toyobo) and sequenced. The pTA2 vector containing requested DNA sequence was digested by NdeI and BamHI and then cloned into a NdeI/BamHI digested pET11a vector (Novagen). The recombinant pET11a vector containing rhIL-1Ra gene was chemically transformed into competent *E. coli* BL21 cells. Transformed cells were identified by digesting the vector pET11a-IL1Ra by Nde I and BamH I simultaneously.

The amino acid sequence of the recombinant human IL-1Ra (rhIL-1Ra) encoded by pET11a-IL1Ra is shown in Table 8, SEQ ID NO:7. This polypeptide comprises the 152 amino acid residues of the mature protein plus an additional methionine required for the expression in the prokaryote system. The predicted molecular weight of recombinant rhIL-1Ra is 17.3 kDa with a PI of 5.4.

TABLE 8

Amino acid sequence of rhIL-1Ra (SEQ ID NO: 7)

MRPSGRKSSKMQAFRIWDVNQKTFYLRNNQLVAGYLQGPNVNLEEKIDVV

PIEPHALFLGIHGGKMCLSCVKSGDETRLQLEAVNITDLSENRKQDKRFA

FIRSDSGPTTSFESAACPGWFLCTAMEADQPVSLTNMPDEGVMVTKFYFQ

EDE

2. The Expression of rhIL-1Ra Protein

A single colony of transformed bacteria was inoculated into LB medium containing 100 μg/mL ampicillin at 37° C. overnight with vigorous shaking A large-scale culture was inoculated using the small-scale culture and at 37° C. for 2 h with vigorous shaking One (1) mM IPTG was used to induce the strain to produce rhIL-1Ra. The incubation continued for additional 4 hours at 37-42° C. and the cell pellets were collected by centrifugation.

Figure 14A:
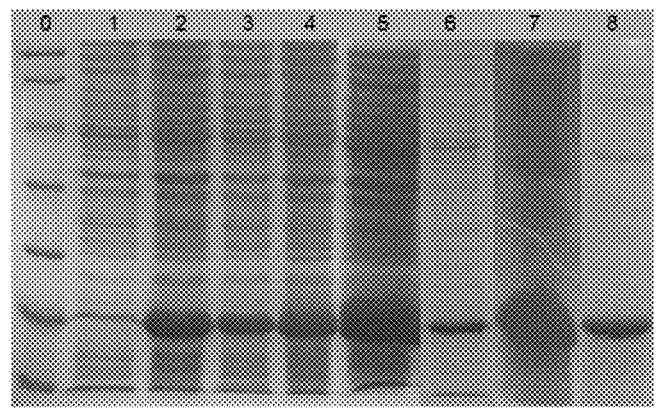
FIGS. 14A-C shows SDS-PAGE analysis of recombinant human IL-1Ra polypeptides.

The insoluble inclusion bodies were harvested by centrifugation after appropriate rounds of homogenization by ultrasonication. The inclusion bodies were solubilized in denaturing buffer (1 mM EDTA, 50 mM NaCl, 0.1 mM PMSF, 8M Urea, 50 mM Tris-HCl, pH 8.0), and refolded by slowly diluting 10-fold into the refolding buffer (20 mM Tris-HCl, 1 mM EDTA, 50 mM NaCl, pH10.7). The protein solution was diluted in an equal volume of diluting buffer (1 mM EDTA, 20 mM Tris-HCl, pH 8.0) and adjusted to pH 9.0. After centrifugation, the supernatant was collected and named rhIL-1RaIB. The rhIL-1Ra was precipitated with ammonium sulfate (0.284 g per mL of supernatant). Precipitated protein was solubilized 10-fold loading buffer 1 (1 mM EDTA, 20 mM Tris-HCl, pH 9.0). After centrifugation the supernatant was collected and named as rhIL-1RaST (FIG. 14A, lane 8).

Figure 14B:
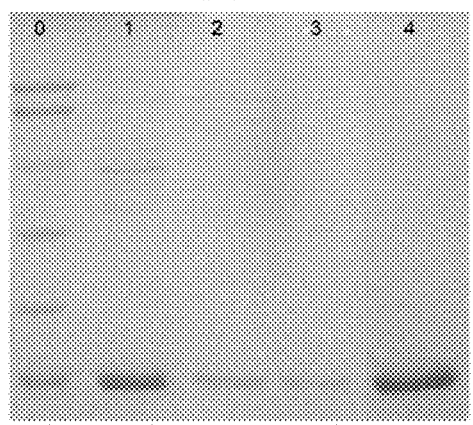
Figure 14C:
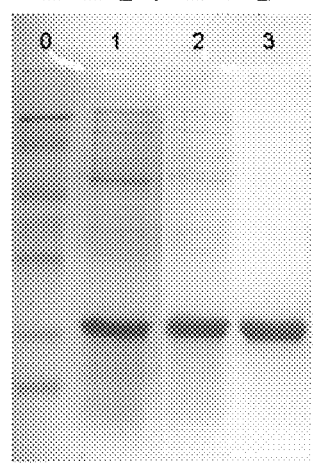

3. The Purification of rhIL-1Ra Protein rhIL-1Ra was further purified by running the solution over DEAE-Sepharose and Q-Sepharose, successively. A 0-1 M NaCl gradient (1%/min) in loading buffer 1 (1 mM EDTA, 20 mM Tris-HCl, pH 9.0) was applied to elute bound rhIL-1Ra from an anion-exchange DEAE-Sepharose (GE) and fractions were collected according to the UV absorption peak. Fractions were assayed for rhIL-1Ra concentration by Commassie-Blue staining after SDS-PAGE (FIG. 14B, lane 2; FIG. 14C, lane 1). Fractions containing rhIL-1Ra were mixed together and adjusted to pH 4.5 and diluted 10-fold into loading buffer 2 (32.26 mM HAc, 17.74 mM NaAc, 1 mM EDTA, pH 4.5). After centrifugation the supernatant was applied to a anion-exchange Q-Sepharose (GE Biosciences). A 0-1 M NaCl gradient (1%/min) in loading buffer 2 was applied to elute bound rhIL-1Ra from the column. According to UV absorption peak fractions were collected. The protein concentration and purity was determined by Commassie-Blue staining after SDS-Page (FIG. 14B, lane 4; FIG. 14C, lane 3).

Example 7

Myeloprotective Effects of Human IL-1Ra in a Murine Model

Figure 15A:
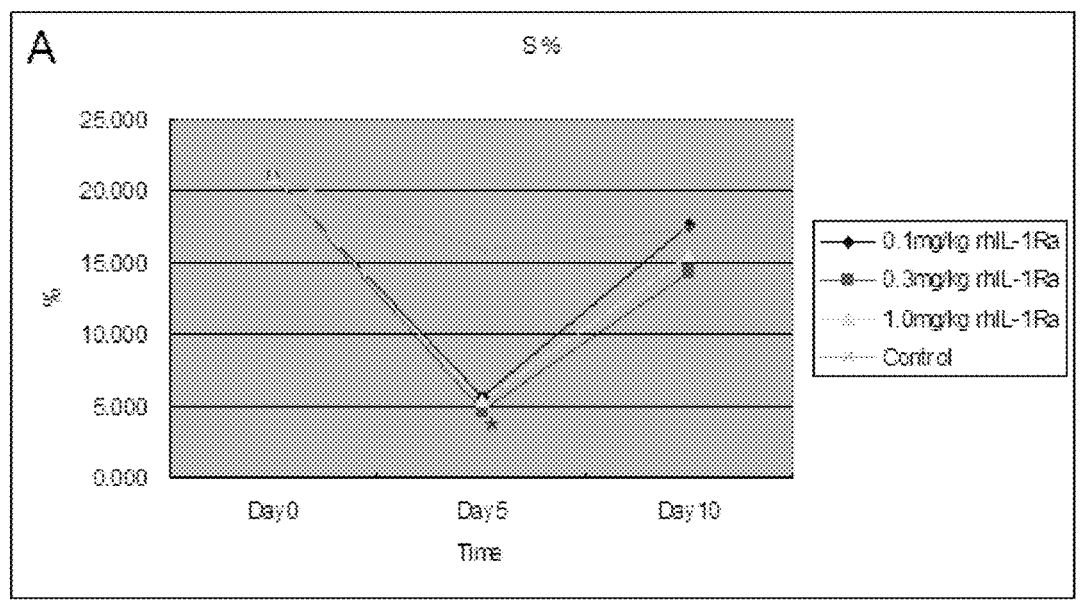
FIGS. 15A-B shows graphs of FACS results indicating the percentage of cells at the S-phase (FIG. 15A) or the $G_0/G_1$ phase (FIG. 15B) of the cell cycle following administration of rhIL-1Ra to mice.
Figure 15B:
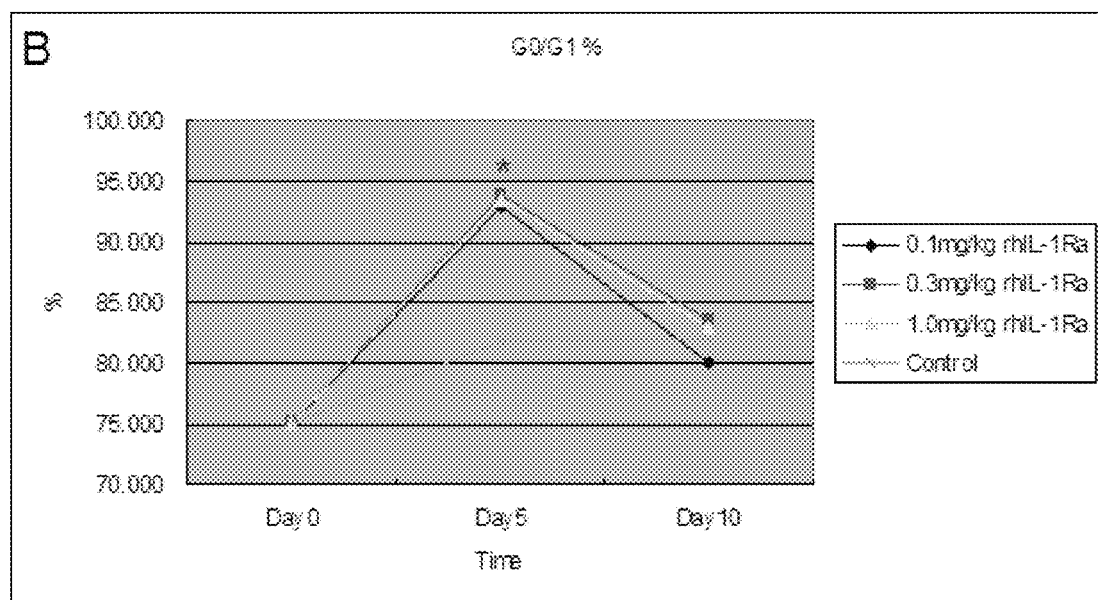
Figure 16:
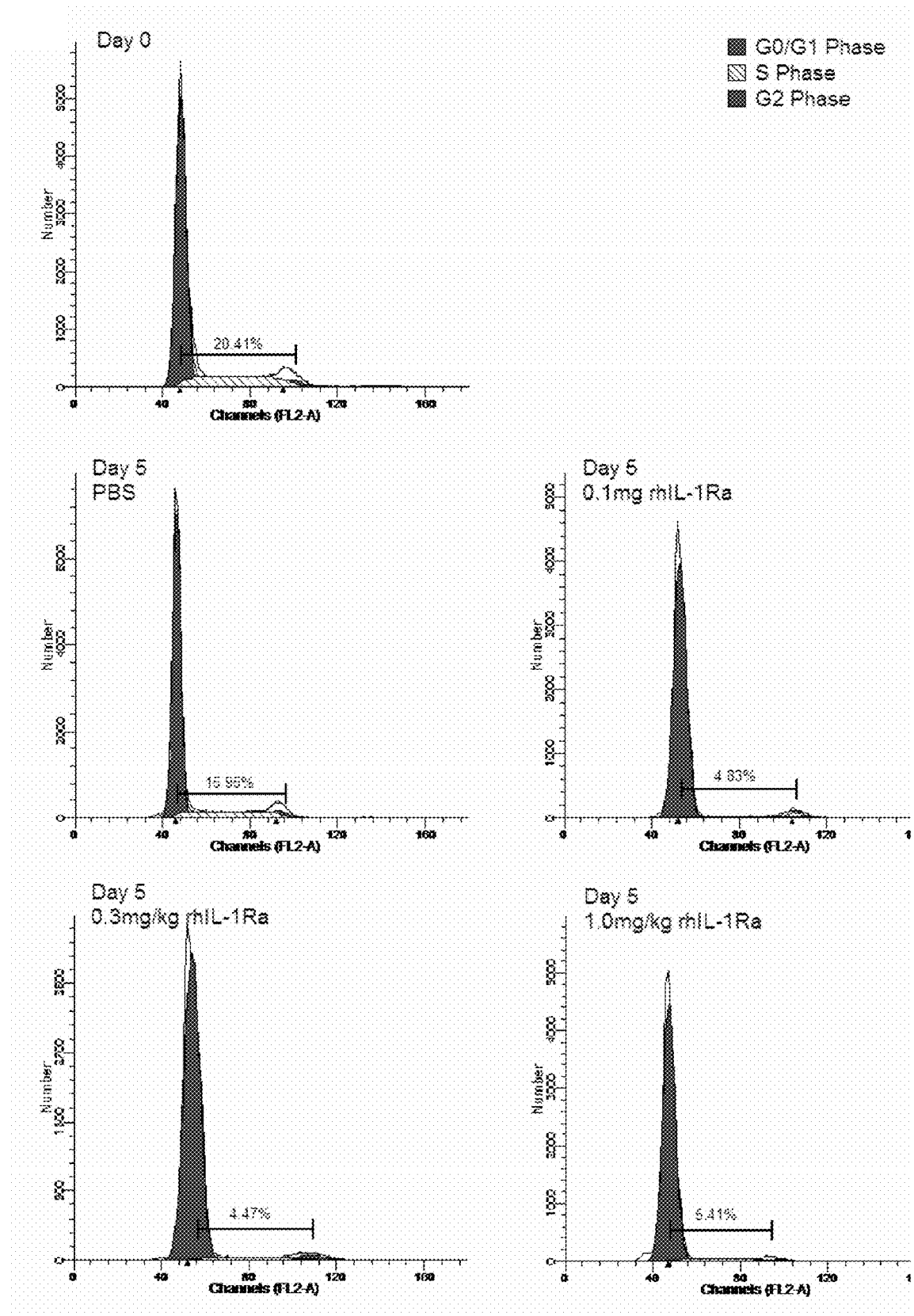
FIG. 16 shows FACS results indicating the percentage of bone marrow cells in the S phase of the cell cycle after 5 days of rhIL-1Ra administration in mice.

To determine the efficacy of human IL-1Ra in a murine model, the effects of rhIL-1Ra on cell cycling of BMMNC (bone marrow mononuclear cells) in normal mice was determined following five consecutive days of injection at three different dosages. rhIL-1Ra was diluted to the desired concentration in PBS, pH 7.4. Normal mice were treated with a daily intraperitoneal injection of rhIL-1Ra for 5 consecutive days at three different doses (0.1, 0.3 and 1 mg/kg of body weight) and were assayed at 5 and 10 days post-treatment. Mice in control group were administered PBS. At days 0, 5 and 10 following rhIL-1Ra treatments, mice were sacrificed by cervical dislocation and their BMMNC were isolated and the cell cycling statuses were analyzed using FACS (BD) (FIG. 15). Results are also shown in Table 9.

rhIL-1Ra either inhibited bone marrow mononuclear cells from entering S-phase (FIG. 15A) or kept them in $G_0/G_1$-phase (FIG. 15B), resulting in the increase of percentage of $G_0/G_1$ phase and the decrease of S-Phase. Statistical differences were calculated by comparing the data with control using 2-tailed Student's t-test. Significant differences with P values <0.01 were indicated by * in the table.

TABLE 9

Effects of rhIL-1Ra on Cell Cycle Status of BMMNC in Mice

| Cell Cycle | Treatment Group | Day After Treatment | | |
|---|---|---|---|---|
| | | 0 | 5 | 10 |
| S Phase | PBS | 21.07% ± 4.07% | 15.90% ± 1.44% | 17.42% ± 5.17% |
| | 0.1 mg/kg rhIL-1Ra | | 5.65% ± 1.26%* | 17.61% ± 1.18% |
| | 0.3 mg/kg rhIL-1Ra | | 4.65% ± 1.64%* | 14.45% ± 2.29% |
| | 1.0 mg/kg rhIL-1Ra | | 5.34% ± 0.69%* | 15.50% ± 0.63% |
| G0/G1 Phase | PBS | 75.11% ± 3.82% | 81.77% ± 0.36% | 82.01% ± 4.86% |
| | 0.1 mg/kg rhIL-1Ra | | 93.04% ± 1.39%* | 80.09% ± 1.15% |
| | 0.3 mg/kg rhIL-1Ra | | 93.84% ± 1.73%* | 83.66% ± 2.36% |
| | 1.0 mg/kg rhIL-1Ra | | 93.53% ± 0.61%* | 82.99% ± 1.01% |

Example 8

Co-Therapy with CXCL9 (Prophetic)

To determine the efficacy of human IL-1Ra and CXCL9 co-therapy in a murine model, the effects of rhIL-1Ra and recombinant human (rhCXCL9) in normal mice and mice administered chemotherapy are measured. The number of peripheral blood and bone marrow cells are measured before and after chemotherapy. Likewise, the effects of rhIL-1Ra and rhCXCL9 coadministration on cell cycling of BMMNC (bone marrow mononuclear cells) in normal mice are determined following up to consecutive days of injection at different dosages. rhIL-1Ra is prepared as described in Example 6. rhCXCL9 is prepared in E. coli and purified as described in PCT/CN2007/000971 (filed Mar. 27, 2007).

For analysis of the effects on cell cycle, rhIL-1Ra and rhCXCL9 are diluted to the desired concentration in PBS, pH 7.4. Normal mice are treated with a daily subcutaneous or intraperitoneal injection of rhIL-1Ra and rhCXCL9 for consecutive days at different doses. Mice in control group are administered PBS. For each of several days following rhIL-1Ra/rhCXCL9 treatments, mice are sacrificed by cervical dislocation and their BMMNC isolated. The cell cycling statuses are analyzed using FACS (BD). The results of the treatment groups are analyzed in comparison to the control. The combination of rhIL-1Ra and rhCXCL9 may be interpreted as having a myelosuppressive effect when the number of bone marrow mononuclear cells entering S-phase is reduced compared to the control.

For analysis of the effects of rhIL-1Ra/rhCXCL9 coadministration on hematological blood cell indices, rhIL-1Ra and rhCXCL9 are diluted to the desired concentration in PBS, pH 7.4. Normal mice are treated with a daily subcutaneous or intraperitoneal injection of rhIL-1Ra and rhCXCL9 for consecutive days at different doses. The mice are then administered a single dose of chemotherapy (250 mg/kg 5-FU). For each of several days following chemotherapy, mice are sacrificed by cervical dislocation. Hematological blood cell indices—peripheral WBC, platelets, and bone marrow cells—are analyzed. The results of the treatment groups are compared to a control not administered the combination therapy. The combination of rhIL-1Ra and rhCXCL9 may be interpreted as having a myeloprotective effect when the hematological blood cell indices are increased following chemotherapy for mice administered the combination compared to mice not administered the combination.

Equivalents

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods and apparatuses within the scope of the invention, in addition to those enumerated herein, will be apparent to those skilled in the art from the foregoing descriptions. Such modifications and variations are intended to fall within the scope of the appended claims. The present invention is to be limited only by the terms of the appended claims, along with the full scope of equivalents to which such claims are entitled. It is to be understood that this invention is not limited to particular methods, reagents, compounds compositions or biological systems, which can, of course, vary. It is also to be understood that the terminology used herein is for the purpose of describing particular embodiments only, and is not intended to be limiting.

Other embodiments are set forth within the following claims.

What is claimed is:

1. A method for providing myeloprotection to a subject in need of chemotherapy, the method comprising:
   (a) administering an effective amount of interleukin-1 receptor antagonist to a subject; and
   (b) following step (a), administering a chemotherapeutic agent to the subject; wherein following the administering of the chemotherapeutic agent, the subject has increased bone marrow cell density, increased platelet level, or increased peripheral white blood cell level compared to a subject not administered the interleukin-1 receptor antagonist.

2. The method of claim 1, wherein the interleukin-1 receptor antagonist is administered subcutaneously.

3. The method of claim 1, wherein the administering of the interleukin-1 receptor antagonist occurs once a day for one to five days prior to the subject receiving the chemotherapeutic agent.

4. The method of claim 1, wherein the administering of the interleukin-1 receptor antagonist occurs once a day for two to five days prior to the subject receiving the chemotherapeutic agent.

5. The method of claim 1, wherein the effective amount is from 0.1 to 10 mg of interleukin-1 receptor antagonist per kg body weight of the subject.

6. The method of claim 1, wherein the effective amount is from 0.5 to 1.5 mg of interleukin-1 receptor antagonist per kg body weight of the subject.

7. The method of claim 1, wherein the interleukin-1 receptor antagonist is human interleukin-1 receptor antagonist.

8. The method of claim 7, wherein the interleukin-1 receptor antagonist is human interleukin-1 receptor antagonist according to SEQ ID NO: 1 or SEQ ID NO: 7.

9. The method of claim 1, wherein the interleukin-1 receptor antagonist is a biologically active variant having at least 95% sequence identity to SEQ ID NO: 1 or SEQ ID NO: 2.

10. The method of claim 1, wherein the chemotherapeutic agent is cell cycle specific.

11. The method of claim 10, wherein the chemotherapeutic agent is selected from the group consisting of 5-fluorouracil, arabinofuranosyl cytidine (Ara-C), vinblastine, and methotrexate.

12. The method of claim 1, wherein the chemotherapeutic agent is cell cycle non-specific.

13. The method of claim 12, wherein the chemotherapeutic agent is selected from the group consisting of: cyclophosphamide, doxorubicin, cisplatin, and busulfan.

14. The method of claim 1, wherein the subject is a human.

15. The method of claim 1, further comprising administering a hematopoietic growth factor to the subject following the chemotherapeutic agent.

16. The method of claim 15, wherein the growth factor is granulocyte-macrophage colony-stimulating factor (GM-CSF) or granulocyte colony-stimulating factor (G-CSF).

* * * * *